(12) United States Patent
Kase et al.

(10) Patent No.: US 12,024,527 B2
(45) Date of Patent: Jul. 2, 2024

(54) COMPOUND HAVING AZABENZOXAZOLE RING STRUCTURE AND ORGANIC ELECTROLUMINESCENT ELEMENT

(71) Applicant: HODOGAYA CHEMICAL CO., LTD., Tokyo (JP)

(72) Inventors: Kouki Kase, Tokyo (JP); Si-In Kim, Tokyo (JP); Ji-Yung Kim, Tokyo (JP); Yuta Hirayama, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 666 days.

(21) Appl. No.: 17/285,405

(22) PCT Filed: Nov. 26, 2019

(86) PCT No.: PCT/JP2019/046248
§ 371 (c)(1),
(2) Date: Apr. 14, 2021

(87) PCT Pub. No.: WO2020/111081
PCT Pub. Date: Jun. 4, 2020

(65) Prior Publication Data
US 2021/0395269 A1 Dec. 23, 2021

(30) Foreign Application Priority Data
Nov. 29, 2018 (JP) ................. 2018-223635

(51) Int. Cl.
*C07D 498/04* (2006.01)
*H10K 30/30* (2023.01)
(Continued)

(52) U.S. Cl.
CPC ......... *C07D 498/04* (2013.01); *H10K 30/353* (2023.02); *H10K 50/16* (2023.02);
(Continued)

(58) Field of Classification Search
None
See application file for complete search history.

(56) References Cited

U.S. PATENT DOCUMENTS

| 5,639,914 A | 6/1997 | Tomiyama et al. |
| 5,792,557 A | 8/1998 | Nakaya et al. |

(Continued)

FOREIGN PATENT DOCUMENTS

| EP | 2 684 932 A1 | 1/2014 |
| EP | 3 683 852 A1 | 7/2020 |

(Continued)

OTHER PUBLICATIONS

Machine translation of KR-20120140603-A, translation generated Jan. 2024, 22 pages. (Year: 2024).*

(Continued)

*Primary Examiner* — Robert S Loewe
(74) *Attorney, Agent, or Firm* — Birch, Stewart, Kolasch & Birch, LLP

(57) ABSTRACT

An object of the present invention is to provide, as a material for a highly efficient and highly durable organic EL element, an organic compound having excellent properties, including excellent electron-injecting/transporting capability, hole-blocking capability, and high stability in the form of a thin film. Another object of the present invention is to provide a highly efficient and highly durable organic EL element by using this compound. The compound having an azabenzoxazole ring structure of the present invention has excellent heat resistance, and good electron-transporting capability. An organic EL element having an electron-transporting layer, a hole-blocking layer, a light-emitting layer, or an electron-injecting layer including the compound had favorable element characteristics.

6 Claims, 5 Drawing Sheets

(51) Int. Cl.
*H10K 50/16* (2023.01)
*H10K 50/17* (2023.01)
*H10K 85/60* (2023.01)

(52) U.S. Cl.
CPC ......... *H10K 50/171* (2023.02); *H10K 85/615* (2023.02); *H10K 85/654* (2023.02); *H10K 85/656* (2023.02); *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 5,869,199 | A | 2/1999 | Kido |
| 6,878,469 | B2 | 4/2005 | Yoon et al. |
| 9,123,897 | B2 | 9/2015 | Yokoyama et al. |
| 9,199,966 | B2 | 12/2015 | Kim et al. |
| 2005/0065340 | A1 | 3/2005 | Arruda et al. |
| 2008/0138656 | A1 | 6/2008 | Ohrui et al. |
| 2012/0313091 | A1 | 12/2012 | Kang et al. |
| 2021/0253569 | A1* | 8/2021 | Jang ............... C07D 413/10 |

FOREIGN PATENT DOCUMENTS

| | | |
|---|---|---|
| JP | 2005-514382 A | 5/2005 |
| JP | 2008-127315 A | 6/2008 |
| JP | 2013-520410 A | 6/2013 |
| KR | 10-2012-0140603 A | 12/2012 |
| KR | 10-2015-0030294 A | 3/2015 |
| KR | 10-2017-0050048 A | 5/2017 |
| KR | 10-2017-0114790 A | 10/2017 |
| WO | WO 2015/022835 A1 | 2/2015 |
| WO | WO 2019/214681 A1 | 11/2019 |

OTHER PUBLICATIONS

Machine translation of KR-20170050048-A, translation generated Jan. 2024, 23 pages. (Year: 2024).*
Watanabe et al., "Organic LEDs using Hexaphenylbenzene Derivatives", Extended Abstracts of the 50th Meeting, the Japan Society of Applied Physics and Related Societies, 2003, 28p-A-6, pp. 1413.
Endo et al., "Efficient up-conversion of triplet excitons into a singlet state and its application for organic light emitting diodes", Applied Physics Letters, 2011, vol. 98, No. 083302, total 3 pages.
Hosokawa et al., "Development of Styryl-Based Light Emitting Material", Proceedings of the 9th Meeting of the Japan Society of Applied Physics, 2001, pp. 55-61, total 8 pages.
International Search Report for PCT/JP2019/046248 mailed on Feb. 10, 2020.
Tatipaka et al., "Substituted 2-Phenylimidazopyridines: A New Class of Drug Leads for Human African Trypanosomiasis", Journal of Medicinal Chemistry, 2014, vol. 57(1), pp. 828-834.
The Journal of Molecular Electronics and Bioelectronics, the Japan Society of Applied Physics, 2000, vol. 11, No. 1, pp. 13-19, total 4 pages.
Wakimoto, "Optimization of driving lifetime durability in organic LED devices using phosphorescent guest emitter", Proceedings of the 9th Meeting of the Japan Society of Applied Physics, 2001, pp. 23-31, total 5 pages.
Xu et al., "A General and Efficient Synthesis of 2-Substituted Oxazolopyridines", Synlett, 2009, No. 7, pp. 1172-1174, with Supporting Information (24 pages).

* cited by examiner (1) (2) (3)

(4) (5) (6)

(7) (8) (9)

(10) (11) (12)

(13) (14) (15)

(16) (17) (18)

COMPOUND HAVING AZABENZOXAZOLE RING STRUCTURE AND ORGANIC ELECTROLUMINESCENT ELEMENT

TECHNICAL FIELD

The present invention relates to a compound suitable for organic electroluminescent elements (hereinafter referred to simply as organic EL elements), which are self-emissive elements favorably used in various display devices, and also to an element. More particularly, the present invention relates to a compound having an azabenzoxazole ring structure and an organic EL element including the compound.

BACKGROUND ART

Since organic EL elements are self-emissive elements, they have larger brightness and better viewability than elements including liquid crystals, and can thus provide a clearer display. For these reasons, active studies have been carried out on organic EL elements.

In 1987, C. W. Tang et al. of Eastman Kodak Company developed an element having a layered structure in which various functions were assigned to different materials, and thus made a practical organic EL element including organic materials. They made an organic EL element having a layered structure including a layer of a fluorescent substance capable of transporting electrons and a layer of an organic substance capable of transporting holes, and injected both charges into the layer of the fluorescent substance to thereby cause the layer to emit light, and as a result, the organic EL element achieved a luminance as high as 1,000 cd/m$^2$ or more at a voltage of 10 V or less (see Patent Literatures 1 and 2, for example).

Organic EL elements have been heretofore much improved to put them to practical use. Electroluminescent elements have been suggested in which an anode, a hole-injecting layer, a hole-transporting layer, a light-emitting layer, an electron-transporting layer, an electron-injecting layer, and a cathode are sequentially provided on a substrate to subdivide various functions in the multi-layered structure even further, and such electroluminescent elements successfully have high efficiency and durability (see Non-Patent Literature 1, for example).

To further increase luminous efficacy, attempts have been made to utilize triplet excitons, and the utilization of phosphorescent compounds has been investigated (see Non-Patent Literature 2, for example).

Moreover, elements that utilize light emission by thermally activated delayed fluorescence (TADF) have also been developed. In 2011, Adachi et al. from Kyushu University achieved a result of an external quantum efficiency of 5.3% by an element including a thermally activated delayed fluorescence material (see Non-Patent Literature 3, for example).

An light-emitting layer can also be prepared by doping a charge-transporting compound, generally called a host material, with a fluorescent compound, a phosphorescent compound, or a material that radiates delayed fluorescence. As stated in the non-patent literature above, the selection of the organic materials in an organic EL element greatly affects the characteristics of that element, such as efficiency and durability (see Non-Patent Literature 2, for example).

In an organic EL element, the charges injected from both electrodes recombine in the light-emitting layer, thereby producing light emission, and how efficiently the both charges, i.e., the holes and the electrons, are passed to the light-emitting layer is of importance. For this purpose, it is necessary to enhance the electron-injecting capability and increase the electron mobility to increase the probability that holes and electrons recombine in the light-emitting layer. In other words, highly efficient light emission can be achieved, if an environment that increases the probability of the recombination even more can be created by confining holes transported from the anode side in the light-emitting layer, preventing deterioration of the electron-transporting layer, and confining excitons generated in the light-emitting layer. Therefore, the functions of the electron-transporting material are important, and there is a need for an electron-transporting material that has great electron-injecting capability, high electron mobility, high hole-blocking capability, and high durability against holes.

Moreover, with regard to element lifespan, heat resistance and amorphousness of the materials are also important. A material with low heat resistance thermally decomposes, due to heat generated during driving the element, even at a low temperature, and thus the material deteriorates. A film made of a material with low amorphousness causes crystallization thereof even in a short period of time to result in deterioration of the element. Thus, the materials to be used are required to have high heat resistance and good amorphousness.

Tris(8-hydroxyquinoline)aluminum (hereinafter abbreviated as Alq3), which is a typical light emitting material, is also commonly used as an electron-transporting material; however, it provides low electron mobility and has a work function of 5.6 eV, and therefore it cannot be said that Alq3 has sufficient hole-blocking capability.

Compounds having a benzotriazole structure have been suggested as compounds improved in the properties including the electron-injecting capability and the electron mobility (see Patent Literature 3, for example). Elements having an electron-transporting layer including such a compound have the improved properties including luminous efficacy; however, these properties are still insufficient. Therefore, there is a demand for a further decrease in driving voltage and a further increase in luminous efficacy.

Also, 3-(4-biphenylyl)-4-phenyl-5-(4-t-butylphenyl)-1,2,4-triazole (hereinafter abbreviated as TAZ) has been suggested as an electron-transporting material with excellent hole-blocking capability (see Patent Literature 4, for example).

TAZ has a work function as high as 6.6 eV and has high hole-blocking capability. Therefore, TAZ is used for an electron transportable, hole-blocking layer stacked on the cathode side of a fluorescent or phosphorescent light-emitting layer produced by vacuum deposition or coating, and TAZ thus contributes to an increase in the efficiency of an organic EL element (see Non-Patent Literature 4, for example).

However, low electron-transporting capability is a critical problem with TAZ, and it is necessary to combine TAZ with an electron-transporting material having higher electron-transporting capability when producing an organic EL element (see Non-Patent Literature 5, for example).

2,9-dimethyl-4,7-diphenyl-1,10-phenanthroline (BCP), which is known as an electron-transporting material, also has a work function as high as 6.7 eV and has high hole-blocking capability. However, BCP has a glass transition point (Tg) as low as 83° C., which results in poor stability of a thin film made of it, and therefore cannot be said to be capable of sufficiently functioning as a hole-blocking layer.

All of these materials have insufficient stability in the form of a film or have insufficient hole-blocking capability. In order to improve characteristics of an organic EL element, there is a demand for an organic compound that has excellent electron-injecting/transporting capability and hole-blocking capability and also has high stability in the form of a thin film.

CITATION LIST

Patent Literature

Patent Literature 1: U.S. Pat. No. 5,792,557
Patent Literature 2: U.S. Pat. No. 5,639,914
Patent Literature 3: U.S. Pat. No. 9,123,897
Patent Literature 4: U.S. Pat. No. 5,869,199
Patent Literature 5: U.S. Pat. No. 9,199,966
Patent Literature 6: EP2684932
Patent Literature 7: U.S. Pat. No. 6,878,469

Non-Patent Literature

Non-Patent Literature 1: Proceedings of the 9th Meeting of the Japan Society of Applied Physics, pp. 55-61 (2001)
Non-Patent Literature 2: Proceedings of the 9th Meeting of the Japan Society of Applied Physics, pp. 23-31 (2001)
Non-Patent Literature 3: Appl. Phys. Lett., 98, 083302 (2011)
Non-Patent Literature 4: Extended Abstracts of the 50th Meeting, the Japan Society of Applied Physics and Related Societies, 28p-A-6, p. 1413 (2003)
Non-Patent Literature 5: The Journal of Molecular Electronics and Bioelectronics, the Japan Society of Applied Physics, Vol. 11, No. 1, pp. 13-19 (2000)
Non-Patent Literature 6: Synlett. 2009 (7), 1172-1174.

SUMMARY OF INVENTION

An object of the present invention is to provide, as a material for a highly efficient and highly durable organic EL element, an organic compound having excellent properties, including excellent electron-injecting/transporting capability, hole-blocking capability, and high stability in the form of a thin film. Furthermore, another object of the present invention is to provide a highly efficient and highly durable organic EL element by using this compound.

An organic compound to be provided by the present invention should have the following physical properties: (1) good electron-injecting properties, (2) high electron mobility, (3) excellent hole-blocking capability, (4) stability in the form of a thin film, and (5) excellent heat resistance. Moreover, an organic EL element to be provided by the present invention should have the following physical characteristics: (1) high luminous efficacy and high power efficiency, (2) a low voltage for the start of light emission, (3) a low driving voltage in actual use, and (4) a long lifespan.

To achieve the above-described objects, the inventors of the present invention have focused on the properties of the azabenzoxazole ring, which has affinity for electrons, and specifically focused on the capability of its nitrogen atoms to coordinate a metal and also on excellent heat resistance. The inventors have thus designed and chemically synthesized compounds having an azabenzoxazole ring structure, and then experimentally produced various organic EL elements including the compounds, followed by thoroughly evaluating the characteristics thereof, and thus, the present invention has been accomplished.

1) Specifically, the present invention provides a compound having an azabenzoxazole ring structure and being represented by the general formula (a-1):

[Chem. 1]

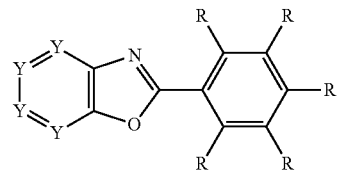

(a-1)

where R is the same or different, and each represents a group represented by the structural formula (b-1), a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted fused polycyclic aromatic group, a linear or branched alkyl group having 1 to 6 carbon atoms and optionally having a substituent, a cycloalkyl group having 5 to 10 carbon atoms and optionally having a substituent, a linear or branched alkenyl group having 2 to 6 carbon atoms and optionally having a substituent, a linear or branched alkyloxy group having 1 to 6 carbon atoms and optionally having a substituent, or a cycloalkyloxy group having 5 to 10 carbon atoms and optionally having a substituent; and Y is the same or different, and each represents a carbon atom having R or a nitrogen atom;

provided that at least one R is a group represented by the structural formula (b-1), and that at least one Y is a nitrogen atom,

[Chem. 2]

----L-Het (b-1)

where L represents a single bond, or a divalent group of a substituted or unsubstituted aromatic hydrocarbon group, a substituted or unsubstituted aromatic heterocyclic group, or a substituted or unsubstituted fused polycyclic aromatic group;

Het represents a substituted or unsubstituted pyridyl group, a substituted or unsubstituted pyrimidyl group, a substituted or unsubstituted triazyl group, a substituted or unsubstituted quinolyl group, a substituted or unsubstituted isoquinolyl group, a substituted or unsubstituted phenanthrolinyl group, a substituted or unsubstituted indolyl group, a substituted or unsubstituted azafluorenyl group, a substituted or unsubstituted diazafluorenyl group, a substituted or unsubstituted azaspirobifluorenyl group, or a substituted or unsubstituted diazaspirobifluorenyl group; and the dashed line represents a binding site.

2) The present invention also provides the compound having an azabenzoxazole ring structure as set forth in clause 1), wherein the compound is represented by the general formula (a-2):

[Chem. 3]

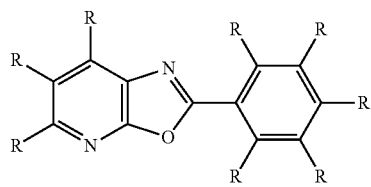

(a-2)

where R is as defined in the general formula (a-1).
3) The present invention also provides the compound having an azabenzoxazole ring structure as set forth in clause 1), wherein the compound is represented by the general formula (a-3):

[Chem. 4]

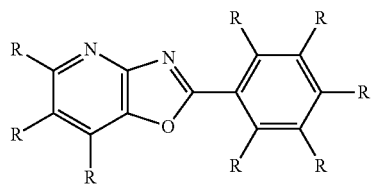

(a-3)

where R is as defined in the general formula (a-1).
4) The present invention also provides the compound having an azabenzoxazole ring structure as set forth in clause 1), wherein the compound is represented by the general formula (a-4):

[Chem. 5]

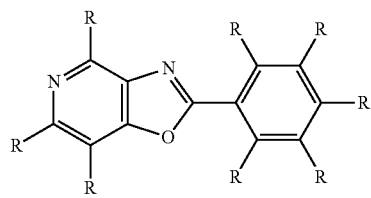

(a-4)

where R is as defined in the general formula (a-1).
5) The present invention also provides the compound having an azabenzoxazole ring structure as set forth in clause 1), wherein the compound is represented by the general formula (a-5):

[Chem. 6]

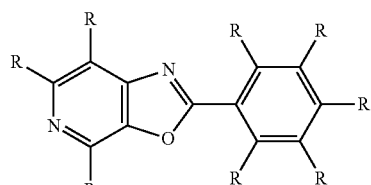

(a-5)

where R is as defined in the general formula (a-1).
6) The present invention also provides the compound having an azabenzoxazole ring structure as set forth in clause 1), wherein the compound is represented by the general formula (a-6) or (a-7):

[Chem. 7]

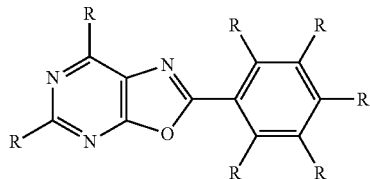

(a-6)

[Chem. 8]

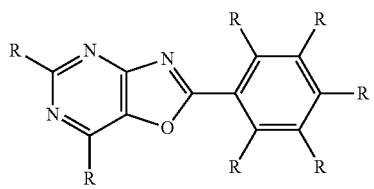

(a-7)

where R is as defined in the general formula (a-1).
7) The present invention also provides the compound having an azabenzoxazole ring structure as set forth in any one of clauses 2) to 6), wherein L in the structural formula (b-1) represents a single bond, a substituted or unsubstituted phenyl group, a substituted or unsubstituted biphenylyl group, or a substituted or unsubstituted naphthyl group.
8) The compound having an azabenzoxazole ring structure as set forth in clause 7),
wherein Het in the structural formula (b-1) represents a substituted or unsubstituted pyridyl group, a substituted or unsubstituted pyrimidyl group, a substituted or unsubstituted quinolyl group, a substituted or unsubstituted isoquinolyl group, or a substituted or unsubstituted phenanthrolinyl group.
9) An organic EL element comprising a pair of electrodes and one or more organic layers sandwiched therebetween,
wherein the compound having an azabenzoxazole ring structure as set forth in any one of clauses 1) to 8) is included in at least one of the organic layers as a constituent material thereof.
10) The organic EL element as set forth in clause 9),
wherein the organic layer including the compound having an azabenzoxazole ring structure is an electron-transporting layer.
11) The organic EL element as set forth in clause 9),
wherein the organic layer including the compound having an azabenzoxazole ring structure is a hole-blocking layer.
12) The organic EL element as set forth in clause 9) above,
wherein the organic layer including the compound having an azabenzoxazole ring structure is a light-emitting layer.
13) The organic EL element as set forth in clause 9) above,
wherein the organic layer including the compound having an azabenzoxazole ring structure is an electron-injecting layer.

Specific examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by R in the general formula (a-1) include a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzooxazolyl group, a benzothiazolyl group, an azafluorenyl group, a diazafluorenyl group, an azaspirobifluorenyl group, a diazaspirobifluorenyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group; and also an aryl group having 6 to 30 carbon atoms, and a heteroaryl group having 2 to 20 carbon atoms.

Specific examples of the "substituent" of the "substituted aromatic hydrocarbon group", the "substituted aromatic heterocyclic group", or the "substituted fused polycyclic aromatic group" represented by R in the general formula (a-1) include a deuterium atom, a cyano group, and a nitro group; halogen atoms such as a fluorine atom, a chlorine atom, a bromine atom, and an iodine atom; silyl groups such as a trimethylsilyl group and a triphenylsilyl group; linear or branched alkyl groups having 1 to 6 carbon atoms such as a methyl group, an ethyl group, and a propyl group; linear or branched alkyloxy groups having 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or fused polycyclic aromatic groups such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; and aromatic heterocyclic groups such as a pyridyl group, a thienyl group, a furyl group, a pyrrolyl group, a quinolyl group, an isoquinolyl group, a benzofuranyl group, a benzothienyl group, an indolyl group, a carbazolyl group, a benzooxazolyl group, a benzothiazolyl group, a quinoxalinyl group, a benzimidazolyl group, a pyrazolyl group, a dibenzofuranyl group, a dibenzothienyl group, and a carbolinyl group. These substituents may further be substituted by any of the substituents listed above as examples. Moreover, such a substituent and the benzene ring substituted therewith, or a plurality of substituents that substitute the same benzene ring may be bonded to each other to form a ring via a single bond, a substituted or unsubstituted methylene group, an oxygen atom, or a sulfur atom.

Specific examples of the "carbon atom having a linear or branched alkyl group having 1 to 6 carbon atoms", the "carbon atom having a cycloalkyl group having 5 to 10 carbon atoms", or the "carbon atom having a linear or branched alkenyl group having 2 to 6 carbon atoms" of the "carbon atom having a linear or branched alkyl group having 1 to 6 carbon atoms and optionally having a substituent", the "carbon atom having a cycloalkyl group having 5 to 10 carbon atoms and optionally having a substituent", or the "carbon atom having a linear or branched alkenyl group having 2 to 6 carbon atoms and optionally having a substituent" represented by R in the general formula (a-1) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group. Such a substituent and the benzene ring substituted therewith, or a plurality of the substituents that substitute the same benzene ring may be bonded to each other to form a ring via a single bond, a substituted or unsubstituted methylene group, a substituted or unsubstituted amino group, an oxygen atom, or a sulfur atom.

Examples of the "substituent" of the "linear or branched alkyl group having 1 to 6 carbon atoms and optionally having a substituent", the "cycloalkyl group having 5 to 10 carbon atoms and optionally having a substituent", or the "linear or branched alkenyl group having 2 to 6 carbon atoms and optionally having a substituent" represented by R in the general formula (a-1) are the same as those listed above as examples of the "substituent" of the "substituted aromatic hydrocarbon group", the "substituted aromatic heterocyclic group", or the "substituted fused polycyclic aromatic group" represented by R in the general formula (a-1). The same holds true for the form that the substituent may be in.

Specific examples of the "carbon atom having a linear or branched alkyloxy group having 1 to 6 carbon atoms" or the "carbon atom having a cycloalkyloxy group having 5 to 10 carbon atoms" of the "carbon atom having a linear or branched alkyloxy group having 1 to 6 carbon atoms and optionally having a substituent" or the "carbon atom having a cycloalkyloxy group having 5 to 10 carbon atoms and optionally having a substituent" represented by R in the general formula (a-1) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group. Such a substituent and the benzene ring substituted therewith, or a plurality of the substituents that substitute the same benzene ring may be bonded to each other to form a ring via a single bond, a substituted or unsubstituted methylene group, a substituted or unsubstituted amino group, an oxygen atom, or a sulfur atom.

Examples of the "substituent" of the "linear or branched alkyloxy group having 1 to 6 carbon atoms and optionally having a substituent" or the "cycloalkyloxy group having 5 to 10 carbon atoms and optionally having a substituent" represented by R in the general formula (a-1) are the same as those listed above as examples of the "substituent" of the "substituted aromatic hydrocarbon group", the "substituted aromatic heterocyclic group", or the "substituted fused polycyclic aromatic group" represented by R in the general formula (a-1). The same holds true for the form that the substituent may be in.

Examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by L in the structural formula (b-1) are similar to those listed above as examples of the "aromatic hydrocarbon group", the "aromatic heterocyclic group", or the "fused polycyclic aromatic group" of the "substituted or unsubstituted aromatic hydrocarbon group", the "substituted or unsubstituted aromatic heterocyclic group", or the "substituted or unsubstituted fused polycyclic aromatic group" represented by R in the general formula (a-1). The same holds true for the form that the substituent may be in.

Examples of the "substituent" of the "substituted aromatic hydrocarbon group", the "substituted aromatic heterocyclic group", or the "substituted fused polycyclic aromatic group" represented by L in the structural formula (b-1) are the same as those listed above as examples of the "substituent" of the "substituted aromatic hydrocarbon group", the "substituted aromatic heterocyclic group", or the "substituted fused polycyclic aromatic group" represented by R in the general formula (a-1). The same holds true for the form that the substituent may be in.

Examples of the "substituent" of the "substituted pyridyl group", the "substituted pyrimidyl group", the "substituted triazyl group", the "substituted quinolyl group", the "substituted isoquinolyl group", the "substituted phenanthrolinyl group", the "substituted indolyl group", the "substituted azafluorenyl group", the "substituted diazafluorenyl group", the "substituted azaspirobifluorenyl group", or the "substituted diazaspirobifluorenyl group" represented by Het in the structural formula (b-1) are the same as those listed above as examples of the "substituent" of the "substituted aromatic hydrocarbon group", the "substituted aromatic heterocyclic group", or the "substituted fused polycyclic aromatic group" represented by R in the general formula (a-1). The same holds true for the form that the substituent may be in.

In the general formula (a-1), R in the case where it is a group other than the group represented by structural formula (b-1) is preferably a hydrogen atom, or the "substituted or unsubstituted fused polycyclic aromatic group".

The "substituted or unsubstituted fused polycyclic aromatic group" is preferably a substituted or unsubstituted naphthyl group, anthracenyl group, phenanthrenyl group, fluorenyl group, or spirobifluorenyl group, and more preferably a substituted or unsubstituted anthracenyl group or spirobifluorenyl group. If these groups have a substituent, the substituent is preferably a phenyl group, a biphenylyl group, a terphenylyl group, a naphthyl group, a phenanthrenyl group, or an anthracenyl group, and more preferably a phenyl group or a naphthyl group.

Preferable specific examples of R in the general formula (a-1) include the groups represented by the following structure:

[Chem. 9]

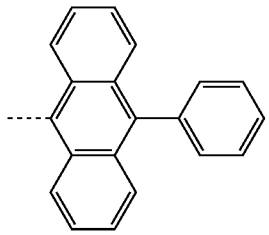

-continued

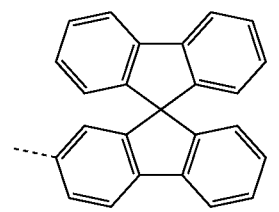

where the dashed line represents a binding site.

L in the structural formula (b-1) is preferably a substituted or unsubstituted phenyl group, biphenylyl group, terphenylyl group, naphthyl group, anthracenyl group, or phenanthrenyl group, and more preferably a substituted or unsubstituted phenyl group, biphenylyl group, or naphthyl group.

Het in the structural formula (b-1) is preferably a substituted or unsubstituted pyridyl group, pyrimidyl group, quinolyl group, isoquinolyl group, or phenanthrolinyl group, and more preferably a substituted or unsubstituted pyridyl group or pyrimidyl group.

Preferable specific examples of the structural formula (b-1) include the groups represented by the following structure:

[Chem. 10]

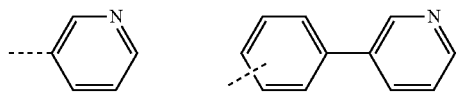

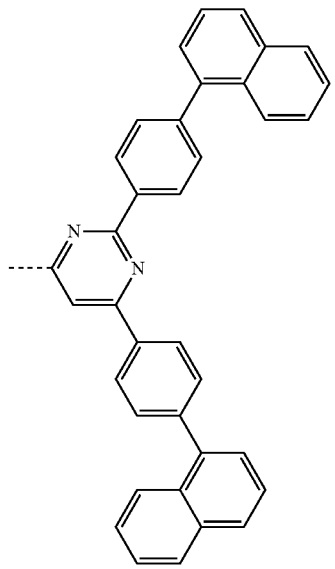

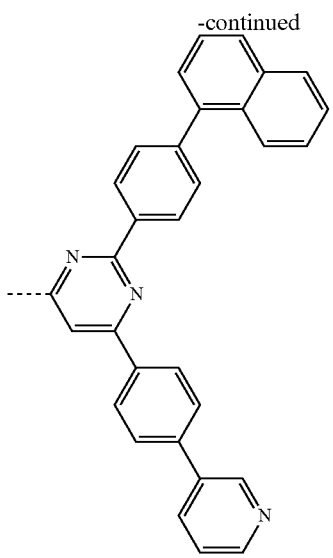

where the dashed line represents a binding site.

The compound having an azabenzoxazole ring structure and represented by the general formula (a-1) are suitable for use in the organic EL element of the present invention, and can be used as a constituent material of an electron-injecting layer, an electron-transporting layer, or a hole-blocking layer of the organic EL element. The compound having an azabenzoxazole ring structure and represented by the general formula (a-1) is particularly preferable as a material of the electron-injecting layer or the electron-transporting layer due to its high electron mobility.

The organic EL element of the present invention includes the compound having an azabenzoxazole ring structure and represented by the general formula (a-1), which has excellent electron-injecting/transporting capability, excellent stability in the form of a thin film, and excellent durability. Therefore, compared with a conventional organic EL element, the organic EL element of the present invention has improved efficiency in terms of transporting electrons from the electron-transporting layer to the light-emitting layer and hence improved luminous efficacy, as well as a reduced driving voltage and hence improved durability of the organic EL element, and thus the organic EL element of the present invention can achieve high efficiency, a low driving voltage, and a long lifespan.

The compound having an azabenzoxazole ring structure of the present invention has the properties including: (1) good electron-injecting properties, (2) high electron mobility, (3) excellent hole-blocking capability, (4) stability in the form of a thin film, and (5) excellent heat resistance. The organic EL element of the present invention has the characteristics including: (6) high luminous efficacy, (7) a low voltage for the start of light emission, (8) a low driving voltage in actual use, and (9) a long lifespan.

The compound having an azabenzoxazole ring structure of the present invention has good electron-injecting properties and high electron mobility. Therefore, an organic EL element having an electron-injecting layer and/or an electron-transporting layer including the compound as an electron-injecting material and/or an electron-transporting material has improved efficiency in terms of transporting electrons to the light-emitting layer and hence improved luminous efficacy, and also has a lower driving voltage and hence improved durability.

The compound having an azabenzoxazole ring structure of the present invention is characterized by excellent hole-blocking capability and electron-transporting capability, stability in the form of a thin film, and capability to confine excitons generated in a light-emitting layer. Therefore, an organic EL element including a hole-blocking layer produced by using the compound as a hole-blocking material has high luminous efficacy because the probability of recombination of holes and electrons is increased to thereby suppress the heat inactivation, and also has an increased maximum luminance because the driving voltage is reduced to thereby improve the current resistance.

The compound having an azabenzoxazole ring structure of the present invention has excellent electron-transporting capability and has a wide band gap. Therefore, an organic EL element including a light-emitting layer prepared by using the compound as a host material has a reduced driving voltage and hence improved luminous efficacy when the light-emitting layer contains a fluorescent emitter, a phosphorescent emitter, or a delayed fluorescent emitter, which are called dopants.

Accordingly, the compound having an azabenzoxazole ring structure of the present invention is useful as the material of an electron-injecting layer, an electron-transporting layer, a hole-blocking layer, or a light-emitting layer of an organic EL element, and can improve the luminous efficacy, the driving voltage, and the durability of a conventional organic EL element.

DESCRIPTION OF EMBODIMENTS

Figure 1:
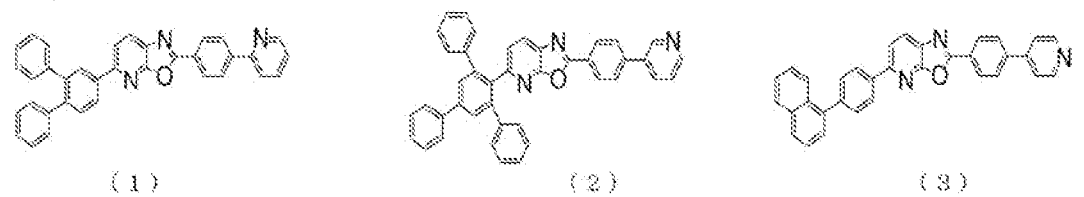
FIG. 1 shows Compounds (1) to (18) as preferable specific examples of the compound having an azabenzoxazole ring structure and represented by the general formula (a-1)
Figure 1:
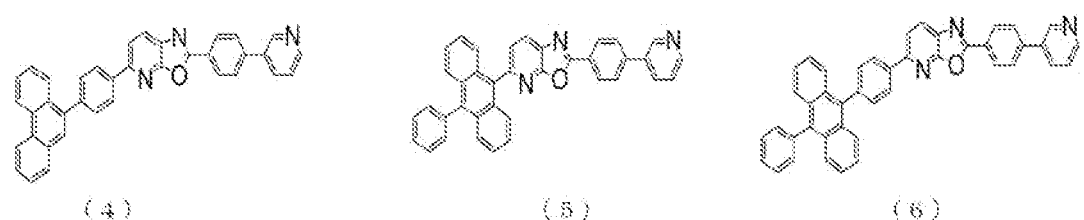
Figure 1:
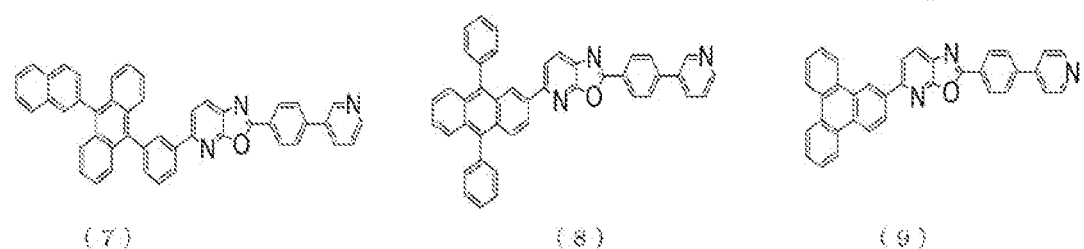
Figure 1:
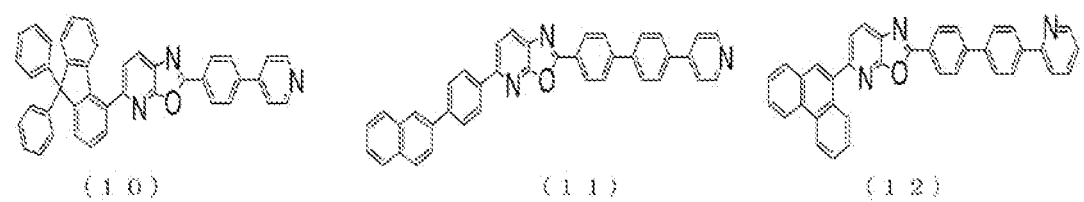
Figure 1:
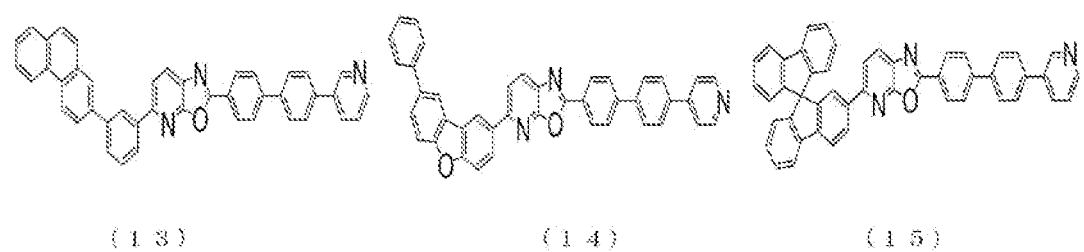
Figure 1:
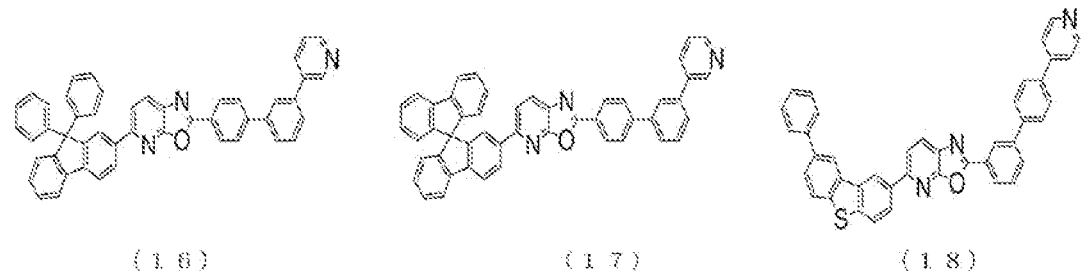
Figure 2:
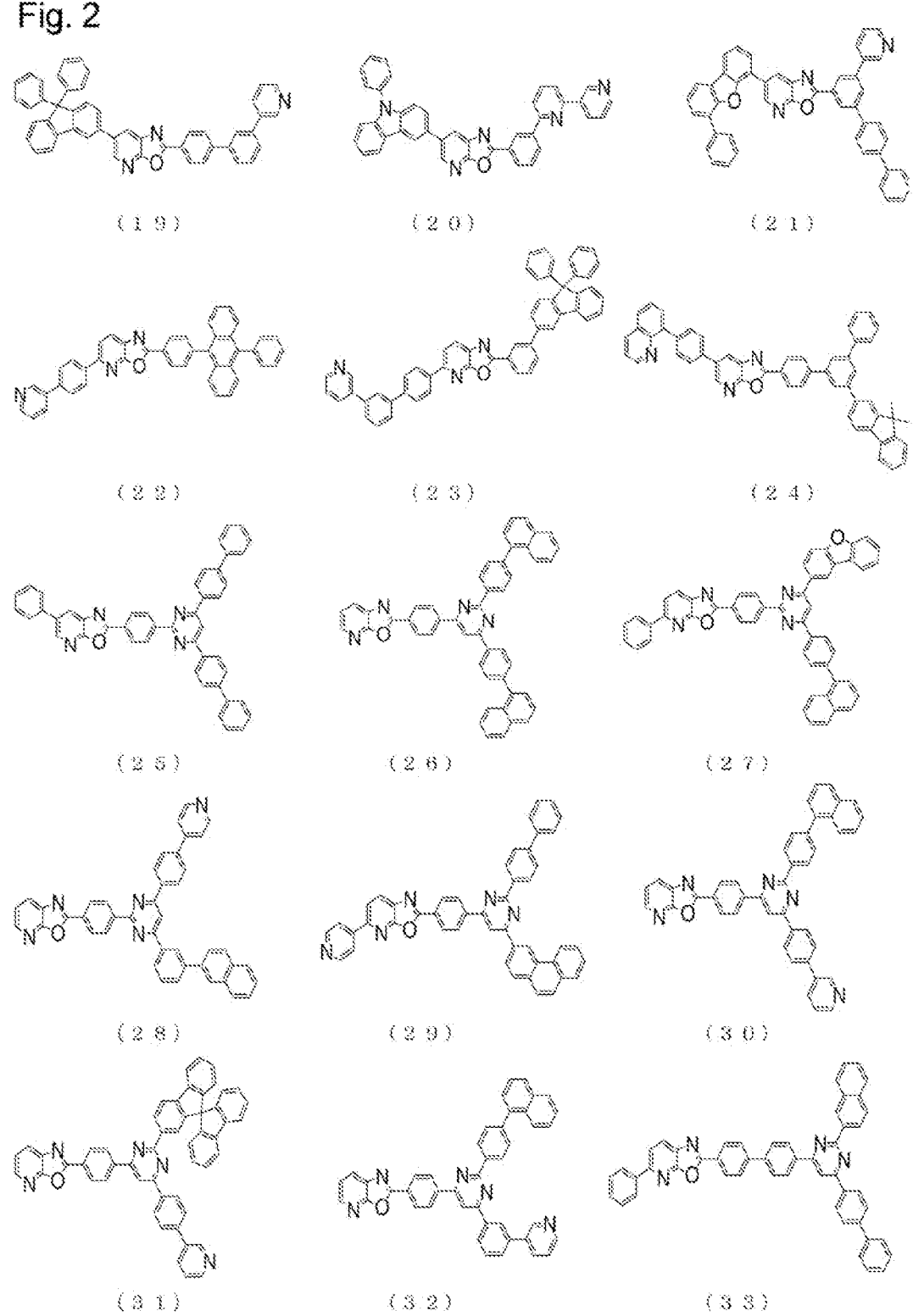
FIG. 2 shows Compounds (19) to (33) as preferable specific examples of the compound having an azabenzoxazole ring structure and represented by the general formula (a-1).
Figure 3:
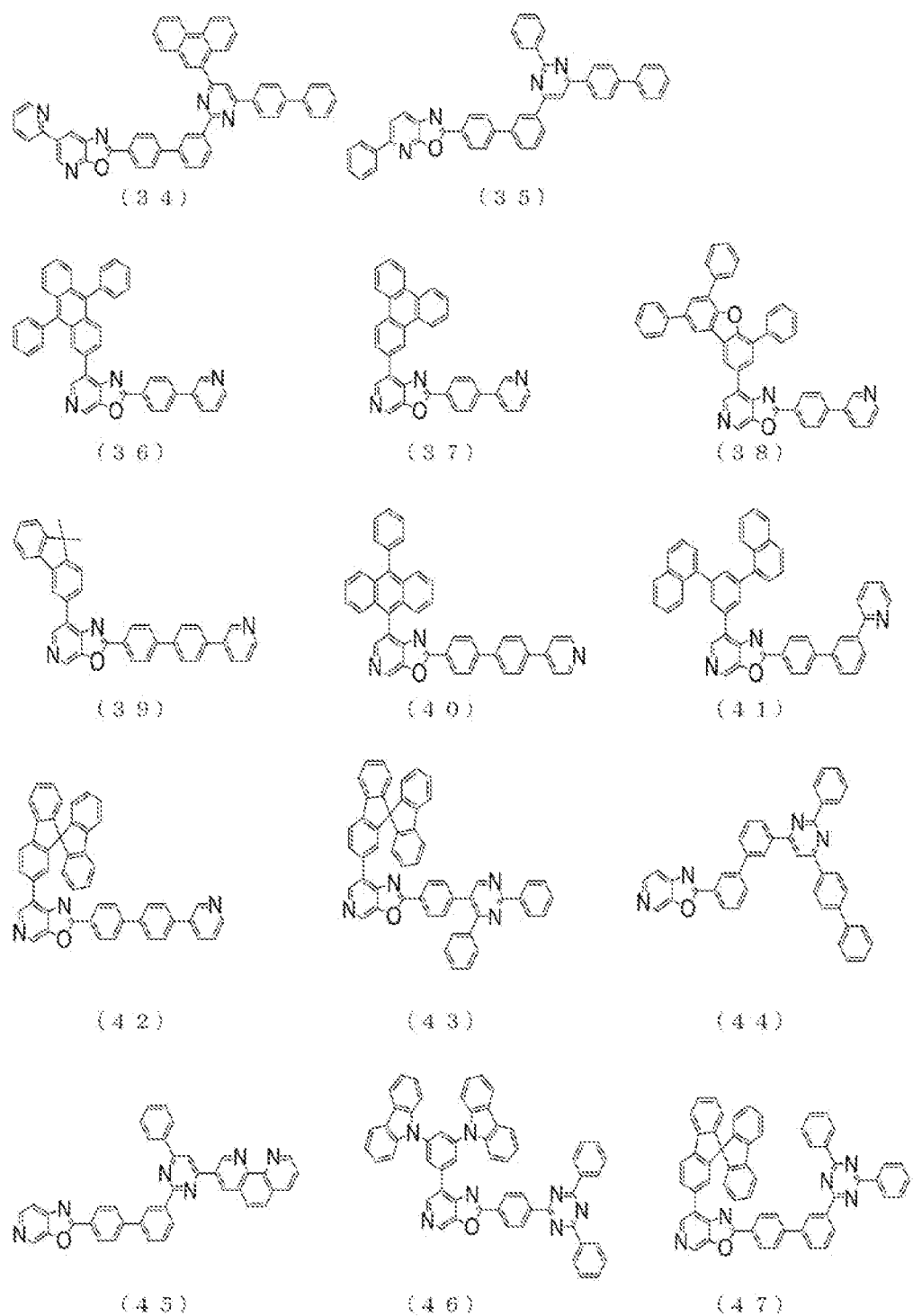
FIG. 3 shows Compounds (34) to (47) as preferable specific examples of the compound having an azabenzoxazole ring structure and represented by the general formula (a-1).
Figure 4:
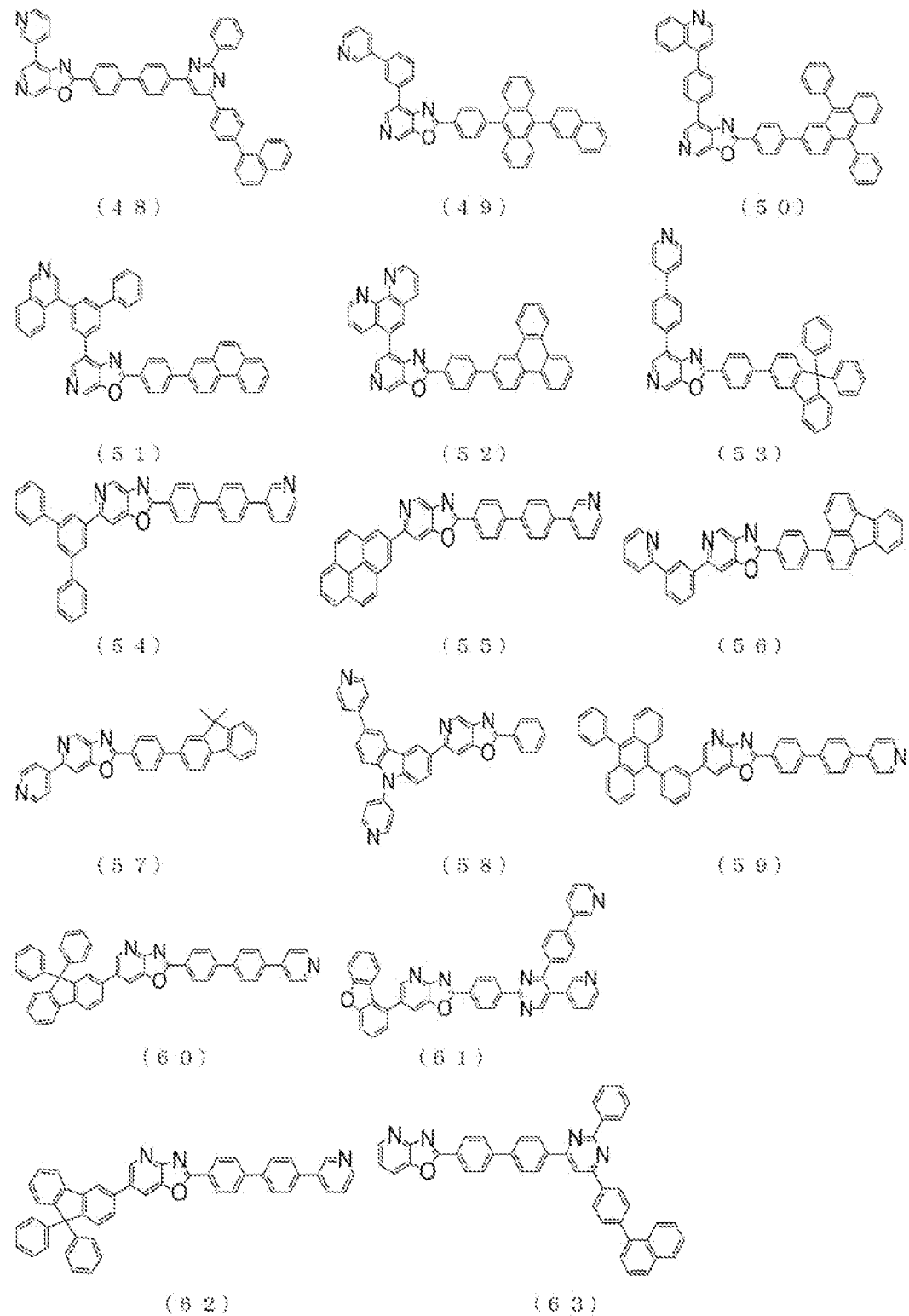
FIG. 4 shows Compounds (48) to (63) as preferable specific examples of the compound having an azabenzoxazole ring structure and represented by the general formula (a-1).
Figure 5:
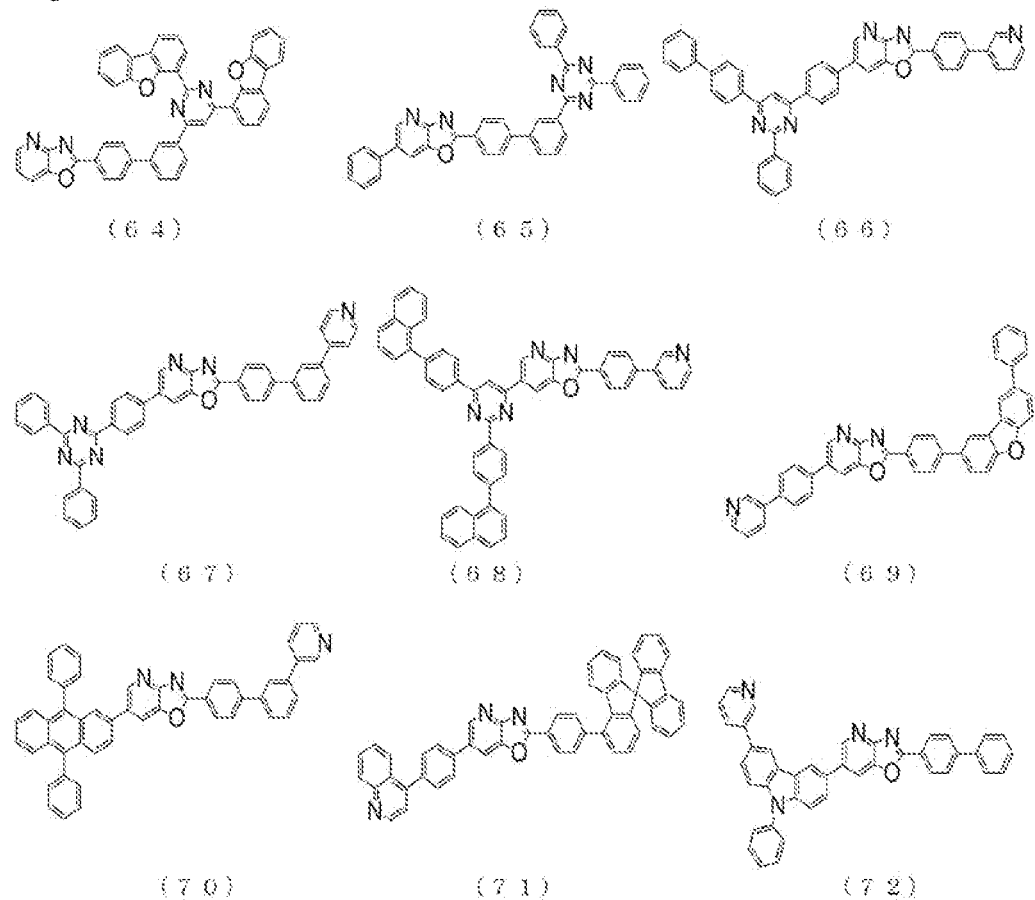
FIG. 5 shows Compounds (64) to (72) as preferable specific examples of the compound having an azabenzoxazole ring structure and represented by the general formula (a-1).

Although the compound having an azabenzoxazole ring structure of the present invention is a novel compound, the compound itself can be synthesized according to a known method (see Non-Patent Literature 6, for example).

Specific preferable examples of the compound having an azabenzoxazole ring structure and represented by the general formula (a-1), which is suitable for use in the organic EL element of the present invention, will be shown in FIGS. 1 to 5. However, the present invention is not limited to these compounds.

The compounds having an azabenzoxazole ring structure and represented by the general formulas (a-1) to (a-7) can be purified using a known purification method such as column chromatography, adsorption with silica gel, activated carbon, activated clay, or others, recrystallization or crystallization from a solvent, or sublimation. The compounds can be identified by NMR analysis. The physical properties can be measured in terms of a melting point, a glass transition point (Tg), a work function, and others. The melting point is a measure of vapor deposition properties, the glass transition point (Tg) is a measure of stability in the form of a thin film, and the work function is a measure of hole-transporting capability and hole-blocking cability.

The melting point and the glass transition point (Tg) can be measured on the compound in the form of a powder using a high-sensitivity differential scanning calorimeter (DSC3100SA manufactured by Bruker AXS K.K.), for example.

The work function can be measured on the compound in the form of a thin film with a thickness of 100 nm formed on an ITO substrate using an ionization potential measuring device (PYS-202 manufactured by Sumitomo Heavy Industries, Ltd.), for example.

The organic EL element of the present invention may have a structure in which an anode, a hole-injecting layer, a hole-transporting layer, a light-emitting layer, an electron-transporting layer, an electron-injecting layer, and a cathode are sequentially provided on a substrate; and the structure may further include an electron-blocking layer between the hole-transporting layer and the light-emitting layer and also may further include a hole-blocking layer between the light-emitting layer and the electron-transporting layer. In these multilayer structures, a single organic layer may perform functions of some layers. For example, a single organic layer may serve as both the hole-injecting layer and the hole-transporting layer, and a single organic layer may serve as both the electron-injecting layer and the electron-transporting layer. Moreover, it is possible to stack two or more organic layers having the same function. Specifically, two hole-transporting layers may be stacked; two light-emitting layers may be stacked; and two electron-transporting layers may be stacked.

An electrode material having a high work function, such as ITO or gold, is used for the anode of the organic EL element of the present invention. Examples of a material used for the hole-injecting layer of the organic EL element of the present invention include porphyrin compounds typified by copper phthalocyanine; starburst triphenylamine derivatives; arylamine compounds having a structure containing two or more triphenylamine structures or carbazolyl structures in the molecule, the triphenylamine or the carbazolyl structures being linked via a single bond or a divalent group having no heteroatom; heterocyclic compounds of acceptor type, such as hexacyanoazatriphenylene; polymer materials of coating type. These materials can be formed into a thin film using a known method such as vapor deposition, spin coating, or inkjet printing.

Examples of a material used for the hole-transporting layer of the organic EL element of the present invention include benzidine derivatives, such as N,N'-diphenyl-N,N'-di(m-tolyl)-benzidine (hereinafter abbreviated as TPD), N,N'-diphenyl-N,N'-di(α-naphthyl)benzidine (hereinafter abbreviated as NPD), and N,N,N',N'-tetrabiphenylyl benzidine; 1,1-bis[(di-4-tolylamino)phenyl]cyclohexane (hereinafter abbreviated as TAPC); and arylamine compounds having a structure containing two or more triphenylamine structures or carbazolyl structures in the molecule, the triphenylamine or the carbazolyl structures being linked via a single bond or a divalent group having no heteroatom.

These materials may be used singly for film formation, or two or more of these material may be mixed and used for film formation. In each case, a single layer may be formed. The hole-transporting layer may have a layered structure composed of different layers each formed of a single kind of the materials described above, a layered structure composed of different layers each formed of a mixture of the materials described above, or a layered structure composed of a layer formed of a single kind of the materials described above and a layer formed of a mixture of two or more of the materials described above.

It is also possible to use, as a material for a hole-injecting/transporting layer, polymer materials of coating type, such as poly(3,4-ethylenedioxythiophene) (hereinafter abbreviated as PEDOT)/poly(styrenesulfonate) (hereinafter abbreviated as PSS)

These materials can be formed into a thin film using a known method such as vapor deposition, spin coating, or inkjet printing.

Other examples of the material used for the hole-injecting layer or the hole-transporting layer include a material obtained by p-doping a material normally used for these layers with trisbromophenylamine hexachloroantimony or a radialene derivative (see Patent Literature 6, for example); and a polymer compound having the structure of a benzidine derivative, such as TPD, as a partial structure thereof.

Examples of a material used for the electron-blocking layer of the organic EL element of the present invention include compounds having an electron-blocking effect, such as carbazole derivatives such as 4,4',4"-tri(N-carbazolyl)triphenylamine (hereinafter abbreviated as TCTA), 9,9-bis[4-(carbazole-9-yl)phenyl]fluorene, 1,3-bis(carbazole-9-yl)benzene (hereinafter abbreviated as mCP), and 2,2-bis(4-carbazole-9-ylphenyl)adamantane (hereinafter abbreviated as Ad-Cz); and compounds having a triphenylsilyl group and a triarylamine structure and typified by 9-[4-(carbazole-9-yl)phenyl]-9-[4-(triphenylsilyl)phenyl]-9H-fluorene. These materials may be used singly for film formation, or a mixture of any of these material and another material may be used to form a single layer.

These materials may be used singly for film formation, or two or more of these material may be mixed and used for film formation. In each case, a single layer may be formed. The electron-blocking layer may have a layered structure composed of different layers each formed of a single kind of the materials described above, a layered structure composed of different layers each formed of a mixture of the materials described above, or a layered structure composed of a layer formed of a single kind of the materials described above and a layer formed of a mixture of two or more of the materials described above. These materials can be formed into a thin film using a known method such as vapor deposition, spin coating, or inkjet printing.

Examples of a material used for the light-emitting layer of the organic EL element of the present invention include the compound having an azabenzoxazole ring structure of the present invention, and also metal complexes of quinolinol derivatives such as $Alq_3$, various types of metal complexes, an anthracene derivative, a bisstyrylbenzene derivative, a pyrene derivative, an oxazole derivative, and a polyphenylene vinylene derivative. The light-emitting layer may include a host material and a dopant material. As the host material, an anthracene derivative is preferably used. Other examples of the host material include the above-listed light-emitting materials including the compound having an azabenzoxazole ring structure of the present invention, and also a heterocyclic compound having an indole ring as a partial structure of a fused ring, a heterocyclic compound having a carbazole ring as a partial structure of a fused ring, a carbazole derivative, a thiazole derivative, a benzimidazole derivative, and a polydialkylfluorene derivative. Examples of the dopant material include quinacridone, coumalin, rubrene, perylene, and derivatives thereof; a benzopyran derivative; a rhodamine derivative; and an aminostyryl derivative.

These materials may be used singly for film formation, or two or more of these material may be mixed and used for film formation. In each case, a single layer may be formed. The light-emitting layer may have a layered structure composed of different layers each formed of a single kind of the materials described above, a layered structure composed of different layers each formed of a mixture of the materials described above, or a layered structure composed of a layer formed of a single kind of the materials described above and a layer formed of a mixture of two or more of the materials described above. These materials can be formed into a thin film using a known method such as vapor deposition, spin coating, or inkjet printing.

A phosphorescent emitter can also be used as a light-emitting material. The phosphorescent emitter may be a metal complex of iridium, platinum, or the like, and examples thereof include a green phosphorescent emitter such as Ir(ppy)$_3$, a blue phosphorescent emitter such as FIrpic or FIr$_6$, and a red phosphorescent emitter such as Btp$_2$Ir (acac). As a host material in this case, a host material having hole injecting/transporting capability may be used, including carbazole derivatives such as 4,4'-di(N-carbazolyl)biphenyl (hereinafter abbreviated as CBP), TCTA, and mCP, and also the compound having an azabenzoxazole ring structure of the present invention. Also, host materials having electron-transporting capability may be used, including p-bis(triphenylsilyl)benzene (hereinafter abbreviated as UGH2) and 2,2',2"-(1,3,5-phenylene)-tris(1-phenyl-1H-benzimidazole) (hereinafter abbreviated as TPBI). Use of these materials enables production of a high-performance organic EL element.

In order to avoid concentration quenching, doping of the host material with a phosphorescent material is preferably performed by co-deposition in an amount within a range of 1 to 30 wt % based on the entire light-emitting layer.

As the light-emitting material, a material that emits delayed fluorescence can also be used, including a CDCB derivative, such as PIC-TRZ, CC2TA, PXZ-TRZ, or 4CzIPN (see Non-Patent Literature 3, for example). These materials can be formed into a thin film using a known method such as vapor deposition, spin coating, or inkjet printing.

Examples of a material used for the hole-blocking layer of the organic EL element of the present invention include the compound having an azabenzoxazole ring structure of the present invention, and also compounds exhibiting a hole-blocking effect including a phenanthroline derivative, such as bathocuproine (hereinafter abbreviated as BCP); a metal complex of a quinolinol derivative, such as BAlq; various types of rare-earth complexes; an oxazole derivative; a triazole derivative; and a triazine derivative. These materials may also serve as the material of the electron-transporting layer.

These materials may be used singly for film formation, or two or more of these material may be mixed and used for film formation. In each case, a single layer may be formed. The hole-blocking layer may have a layered structure composed of different layers each formed of a single kind of the materials described above, a layered structure composed of different layers each formed of a mixture of the materials described above, or a layered structure composed of a layer formed of a single kind of the materials described above and a layer formed of a mixture of two or more of the materials described above. These materials can be formed into a thin film using a known method such as vapor deposition, spin coating, or inkjet printing.

Examples of a material used for the electron-transporting layer of the organic EL element of the present invention include the compound having an azabenzoxazole ring structure of the present invention, and also metal complexes of quinolinol derivatives, such as Alq$_3$ and BAlq; various types of metal complexes; a triazole derivative; a triazine derivative; an oxadiazole derivative; a pyridine derivative; a benzimidazole derivative; a thiadiazole derivative; an anthracene derivative; a carbodiimide derivative; a quinoxaline derivative; a pyridoindole derivative; a phenanthroline derivative; and a silole derivative.

These materials may be used singly for film formation, or two or more of these material may be mixed and used for film formation. In each case, a single layer may be formed. The electron-transporting layer may have a layered structure composed of different layers each formed of a single kind of the materials described above, a layered structure composed of different layers each formed of a mixture of the materials described above, or a layered structure composed of a layer formed of a single kind of the materials described above and a layer formed of a mixture of two or more of the materials described above. These materials can be formed into a thin film using a known method such as vapor deposition, spin coating, or inkjet printing.

Examples of a material used for the electron-injecting layer of the organic EL element of the present invention include the compound having an azabenzoxazole ring structure of the present invention, and also an alkali metal salt such as lithium fluoride or cesium fluoride; an alkaline earth metal salt such as magnesium fluoride; a metal complex of a quinolinol derivative such as lithium quinolinol; a metal oxide such as aluminum oxide; and a metal such as ytterbium (Yb), samarium (Sm), calcium (Ca), strontium (Sr), and cesium (Cs). The electron-injecting layer can however be omitted when an electron-transporting layer and a cathode are suitably selected.

Furthermore, a material obtained by n-doping a material normally used for an electron-injecting layer or an electron-transporting layer with a metal such as cesium can be used for the electron-injecting layer or the electron-transporting layer.

Examples of an electrode material used for the cathode of the organic EL element of the present invention include a metal having a low work function, such as aluminum; and an alloy having an even lower work function, such as a magnesium-silver alloy, a magnesium-indium alloy, and an aluminum-magnesium alloy.

EXAMPLES

Hereinafter, embodiments of the present invention will be described in greater detail by way of Examples. However, the present invention is not limited to Examples below as long as it does not depart from the gist thereof.

Example 1

Synthesis of 6-(10-phenyl-anthracene-9-yl)-2-(4-pyridine-3-yl-phenyl)-7-azabenzoxazole (Compound (5))

First, 4.1 g of 2-(4-chlorophenyl)-6-(10-phenyl-anthracene-9-yl)-7-azabenzoxazole, 1.1 g of 3-pyridylboronic acid, 0.6 g of tris(dibenzylideneacetone)dipalladium(0), 1.0 ml of 50% (w/v) tri-(t-butyl)phosphine solution in toluene, and 5.2 g of cesium carbonate were placed in a reaction vessel, and stirred under reflux overnight in a 1,4-dioxane/H$_2$O mixed solvent. The reaction system was allowed to cool. Then, ethyl acetate/H$_2$O was added thereto, and an organic layer was obtained through extraction and separation, and concentrated to obtain a crude product. The thus obtained crude product was purified by column chromatography (carrier: silica gel, eluent: dichloromethane/ethyl acetate) to thereby obtain 3.2 g (yield: 71%) of a pale yellow powder of 6-(10-phenyl-anthracene-9-yl)-2-(4-pyridine-3-yl-phenyl)-7-azabenzoxazole (Compound (5)).

[Chem. 11]

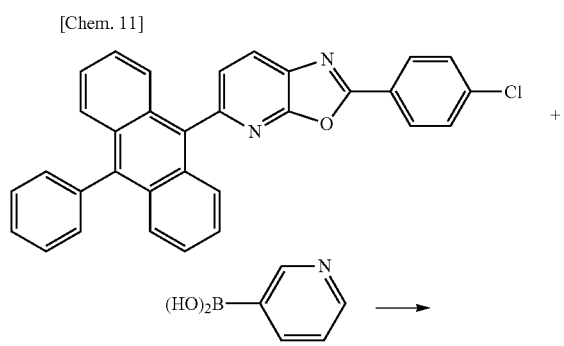

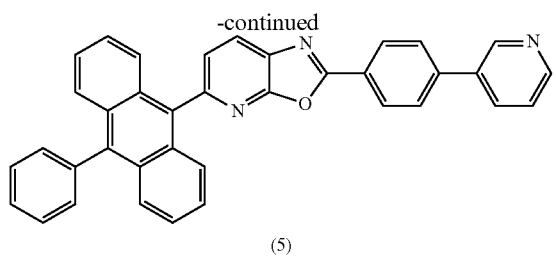

The structure of the obtained pale yellow powder was identified using NMR.

In $^1$H-NMR (CDCl$_3$), the following signals of 23 hydrogens were detected. δ (ppm)=8.99 (1H), 8.70 (1H), 8.50 (2H), 8.36 (1H), 8.01 (1H), 7.85 (2H), 7.79-7.57 (8H), 7.56-7.33 (7H).

Example 2

Synthesis of 2-{4'-(pyridine-3-yl)-biphenyl-4-yl}-6-(9,9'-spirobi[9H]fluorene-2-yl)-7-azabenzoxazole (Compound (15))

First, 10.0 g of 2-(4-chlorophenyl)-6-(9,9'-spirobi[9H]fluorene-2-yl)-7-azabenzoxazole, 4.4 g of 4-(pyridine-3-yl)-phenylboronic acid, 0.5 g of tris(dibenzylideneacetone)dipalladium(0), 0.3 g of tricyclohexylphosphine, and 11.7 g of tripotassium phosphate were placed in a reaction vessel, and stirred under reflux overnight in a 1,4-dioxane/H$_2$O mixed solvent. The reaction system was allowed to cool. Then, ethyl acetate/H$_2$O was added thereto, and an organic layer was obtained through extraction and separation, and concentrated to obtain a crude product. The thus obtained crude product was purified by column chromatography (carrier: silica gel, eluent: dichloromethane/ethyl acetate) to thereby obtain 8.7 g (yield: 71%) of a pale yellow powder of 2-{4'-(pyridine-3-yl)-biphenyl-4-yl}-6-(9,9'-spirobi[9H]fluorene-2-yl)-7-azabenzoxazole (Compound (15)).

[Chem. 12]

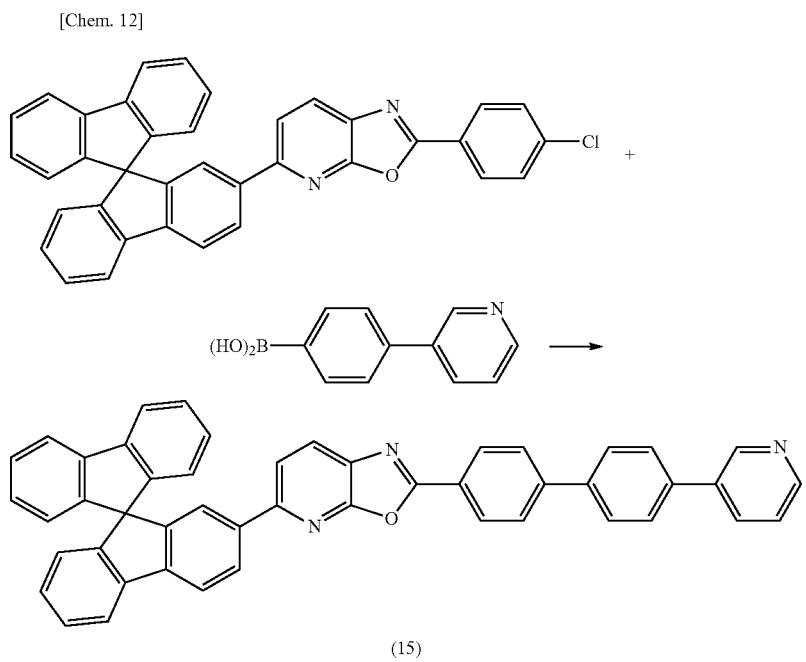

The structure of the obtained pale yellow powder was identified using NMR.

In ¹H-NMR (CDCl₃), the following signals of 29 hydrogens were detected.

δ (ppm)=8.94 (1H), 8.65 (1H), 8.37 (2H), 8.21 (1H), 8.01 (2H), 7.96 (1H), 7.92 (3H), 7.83 (2H), 7.81 (2H), 7.73 (2H), 7.69 (1H), 7.50 (1H), 7.42 (4H), 7.16 (2H), 7.14 (1H), 6.82 (2H), 6.76 (1H).

Example 3

Synthesis of 2-{3'-(pyridine-3-yl)-biphenyl-4-yl}-spirobi[9H]fluorene-2-yl)-7-azabenzoxazole (Compound (17))

First, 10.0 g of 2-(4-chlorophenyl)-6-(9,9'-spirobi[9H]fluorene-2-yl)-7-azabenzoxazole, 4.4 g of 3-(pyridine-3-yl)-phenylboronic acid, 0.5 g of tris(dibenzylideneacetone)dipalladium(0), 0.3 g of tricyclohexylphosphine, 11.7 g of tripotassium phosphate were placed in a reaction vessel, and stirred under reflux overnight in a 1,4-dioxane/H₂O mixed solvent. The reaction system was allowed to cool. Then, ethyl acetate/H₂O was added thereto, and an organic layer was obtained through extraction and separation, and concentrated to obtain a crude product. The thus obtained crude product was purified by column chromatography (carrier: silica gel, eluent: dichloromethane/ethyl acetate) to thereby obtain 8.3 g (yield: 68%) of a pale yellow powder of 2-{3'-(pyridine-3-yl)-biphenyl-4-yl}-spirobi[9H]fluorene-2-yl)-7-azabenzoxazole (Compound (17)).

[Chem. 13]

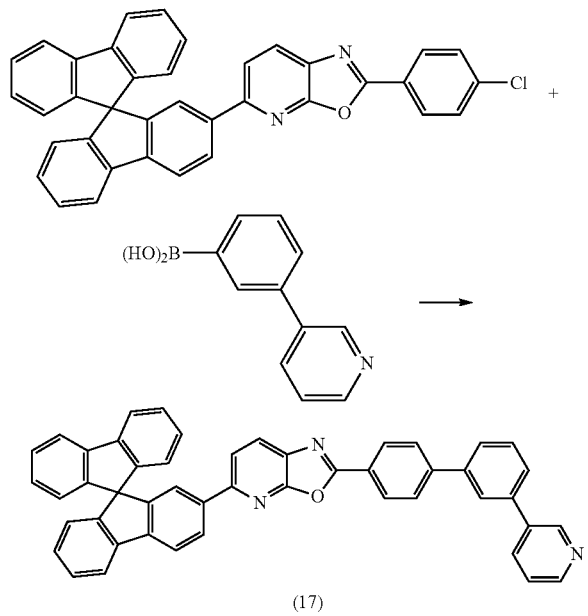

(17)

The structure of the obtained pale yellow powder was identified using NMR.

In ¹H-NMR (CDCl₃), the following signals of 29 hydrogens were detected.

δ (ppm)=8.94 (1H), 8.66 (1H), 8.38 (2H), 8.21 (1H), 8.01 (2H), 7.97 (1H), 7.91 (3H), 7.87 (1H), 7.84 (2H), 7.72 (1H), 7.70 (1H), 7.63 (2H), 7.50 (1H), 7.41 (4H), 7.16 (2H), 7.13 (1H), 6.82 (2H), 6.76 (1H).

Example 4

Synthesis of 2-{4-(10-phenyl-anthracene-9-yl)-phenyl}-6-(4-pyridine-3-yl-phenyl)-7-azabenzoxazole (Compound (22))

First, 8.1 g of 2-(4-chlorophenyl)-6-(4-pyridine-3-yl-phenyl)-7-azabenzoxazole, 6.9 g of 10-phenyl-9-anthraceneboronic acid, 0.6 g of tris(dibenzylideneacetone)dipalladium (0), 4.0 ml of 50% (w/v) tri-(t-butyl)-phosphine solution in toluene, and 13.7 g of cesium carbonate were placed in a reaction vessel, and stirred under reflux overnight in a 1,4-dioxane/H₂O mixed solvent. The reaction system was allowed to cool. Then, methanol was added thereto, and the deposited solid was collected by filtering to thereby obtain a crude product. The thus obtained crude product was purified by column chromatography (carrier: silica gel, eluent: dichloromethane/ethyl acetate) to thereby obtain 4.2 g (yield: 33%) of a yellow powder of 2-{4-(10-phenyl-anthracene-9-yl)-phenyl}-6-(4-pyridine-3-yl-phenyl)-7-azabenzoxazole (Compound (22)).

[Chem. 14]

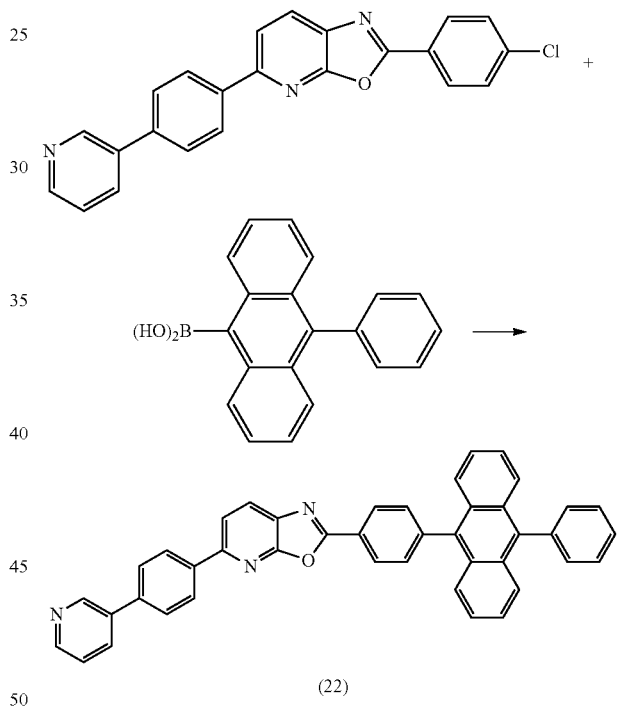

(22)

The structure of the obtained yellow powder was identified using NMR.

In ¹H-NMR (CDCl₃), the following signals of 27 hydrogens were detected.

δ (ppm)=8.98 (1H), 8.66 (1H), 8.60 (2H), 8.29 (2H), 8.24 (1H), 8.02 (1H), 7.97 (1H), 7.84-7.70 (8H), 7.64 (3H), 7.52 (2H), 7.47-7.36 (5H).

Example 5

Synthesis of 2-[4-{2,6-bis(4-naphthalene-1-yl-phenyl)-pyrimidine-4-yl}-phenyl]-7-azabenzoxazole (Compound (26))

First, 4.6 g of 2-{4-(2,6-dichloropyrimidine-4-yl)-phenyl}-7-azabenzoxazole, 7.3 g of 4-(naphthalene-1-yl)-phenylboronic acid, and 0.6 g of tetrakis(triphenylphosphine) palladium(0) were placed in a reaction vessel, and 32 mL of toluene, 8 mL of ethanol, and an aqueous solution of 5.6 g of potassium carbonate in 20 mL of $H_2O$ were added thereto. The resulting mixture was stirred under reflux overnight. The reaction system was allowed to cool. Then, methanol was added thereto, and the deposited solid was collected by filtering to obtain a crude product. The obtained crude product was purified through recrystallization from a monochlorobenzene solvent to thereby obtain 5.8 g (yield: 64%) of a white solid of 2-[4-{2,6-bis(4-naphthalene-1-yl-phenyl)-pyrimidine-4-yl}-phenyl]-7-azabenzoxazole (Compound (26)).

[Chem. 15]

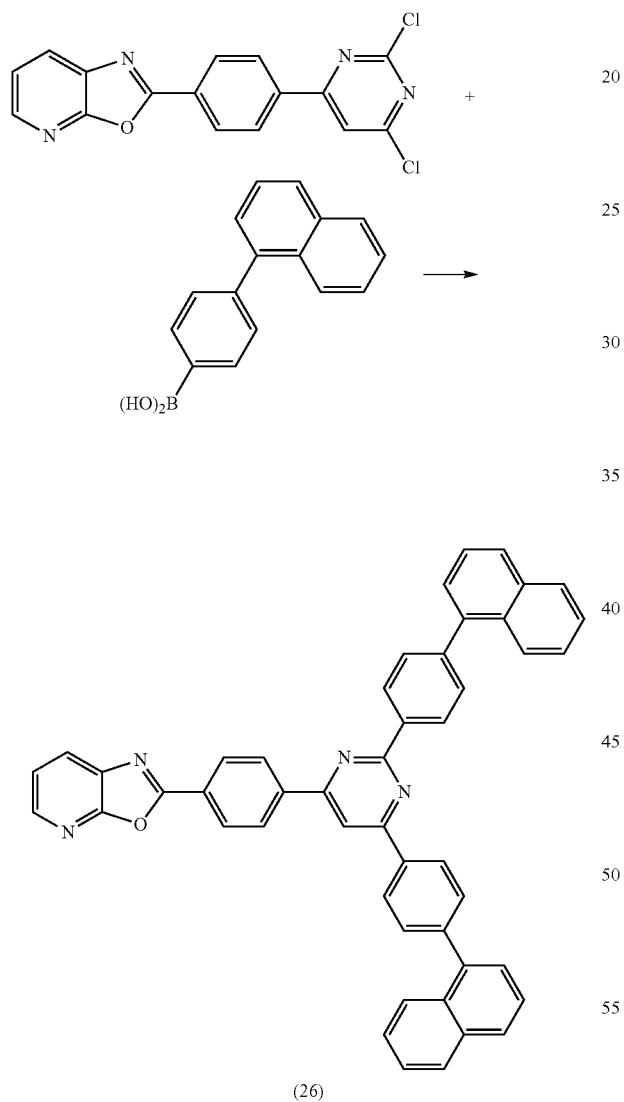

(26)

The structure of the obtained white powder was identified using NMR.

In $^1$H-NMR ($CDCl_3$), the following signals of 30 hydrogens were detected.

δ (ppm)=8.91 (2H), 8.55 (4H), 8.50 (2H), 8.41 (1H), 8.23 (1H), 8.13 (1H), 8.01 (2H), 7.94 (4H), 7.76 (2H), 7.74 (2H), 7.62-7.44 (8H), 7.41 (1H).

Example 6

Synthesis of 2-[4-{2-(4-naphthalene-1-yl-phenyl)-6-(4-pyridine-3-yl-phenyl)-pyrimidine-4-yl}-phenyl]-7-azabenzoxazole (Compound (30))

First, 6.3 g of 2-[4-{2-chloro-6-(4-pyridine-3-yl-phenyl)-pyrimidine-4-yl}-phenyl]-7-azabenzoxazole, 4.1 g of 4-(naphthalene-1-yl)-phenylboronic acid, and 0.3 g of tetrakis(triphenylphosphine)palladium(0) were placed in a reaction vessel, and 44 mL of toluene, 11 mL of ethanol, and an aqueous solution of 2.3 g of potassium carbonate in 8 mL of $H_2O$ were added thereto. The resulting mixture was stirred under reflux overnight. The reaction system was allowed to cool. Then, methanol was added thereto, and the deposited solid was collected by filtering to obtain a crude product. The thus obtained crude product was purified by column chromatography (carrier: silica gel, eluent: dichloromethane/ethyl acetate) to thereby obtain 3.2 g (yield: 37%) of a white solid of 2-[4-{2-(4-naphthalene-1-yl-phenyl)-6-(4-pyridine-3-yl-phenyl)-pyrimidine-4-yl}-phenyl]-7-azabenzoxazole (Compound (30)).

[Chem. 16]

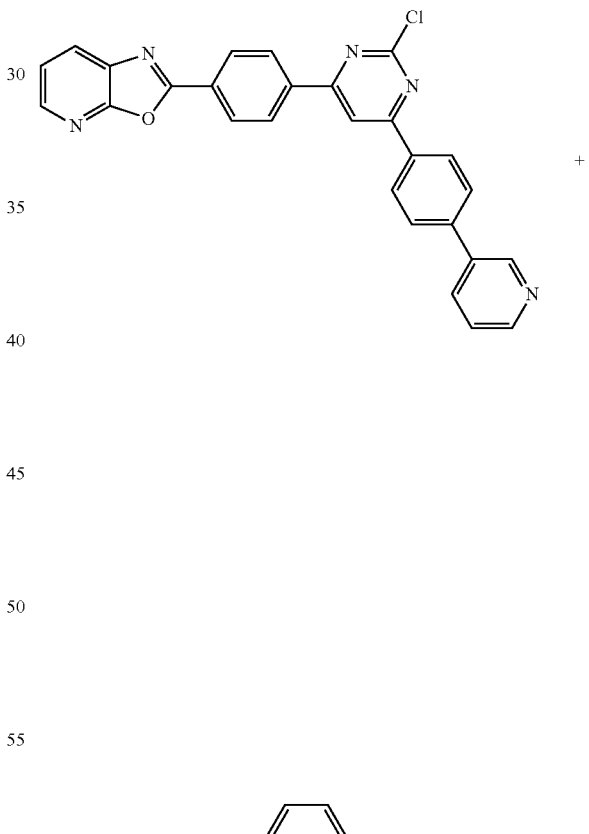

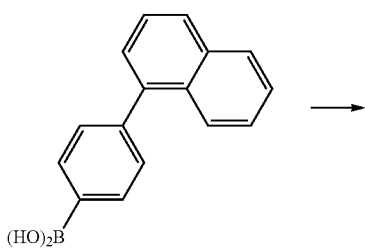

-continued

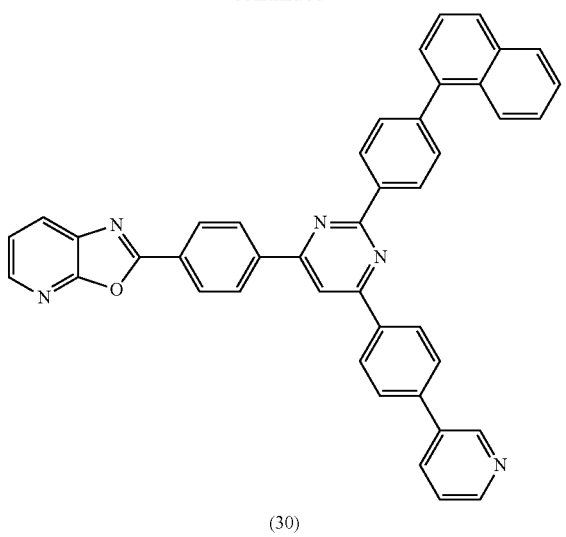

(30)

The structure of the obtained white powder was identified using NMR.

In $^1$H-NMR (CDCl$_3$), the following signals of 27 hydrogens were detected.

δ (ppm)=8.97 (1H), 8.88 (2H), 8.66 (1H), 8.54 (4H), 8.49 (2H), 8.41 (1H), 8.18 (1H), 8.13 (1H), 8.01 (2H), 7.93 (2H), 7.81 (2H), 7.73 (2H), 7.63-7.37 (6H).

Example 7

The melting point and the glass transition point of each of the azabenzoxazole compounds represented by the general formulas (a-1) to (a-7) were measured using a high-sensitivity differential scanning calorimeter (DSC3100SA manufactured by Bruker AXS K.K.). Table 1 shows the results.

TABLE 1

|  | Melting point | Glass transition point |
| --- | --- | --- |
| Compound of Ex. 1 | 342° C. | 134° C. |
| Compound of Ex. 2 | 328° C. | 165° C. |
| Compound of Ex. 3 | — | 146° C. |
| Compound of Ex. 4 | 394° C. | — |
| Compound of Ex. 5 | 271° C. | 135° C. |
| Compound of Ex. 6 | 293° C. | 134° C. |

The compounds having an azabenzoxazole ring structure and represented by the general formulas (a-1) to (a-7) had a glass transition point of at least 130° C., which means that these compounds are stable in the form of a thin film.

Example 8

A vapor-deposited film (thickness: 100 nm) of the compound having an azabenzoxazole ring structure and represented by the general formula (a-1) to (a-7) was formed on an ITO substrate, and the work function was measured using an ionization potential measuring device (PYS-202 manufactured by Sumitomo Heavy Industries, Ltd.). Table 2 shows the results.

TABLE 2

|  | Work function |
| --- | --- |
| Compound of Ex. 1 | 6.07 eV |
| Compound of Ex. 2 | 6.37 eV |
| Compound of Ex. 3 | 6.35 eV |
| Compound of Ex. 4 | 5.91 eV |
| Compound of Ex. 5 | 6.58 eV |
| Compound of Ex. 6 | 6.64 eV |

The compounds having an azabenzoxazole ring structure and represented by the general formulas (a-1) to (a-7) had a work function value greater than 5.5 eV, which is the work function of common hole-transporting materials such as NPD and TPD. This means that these compounds have good hole-blocking capability.

Example 9

Figure 6:
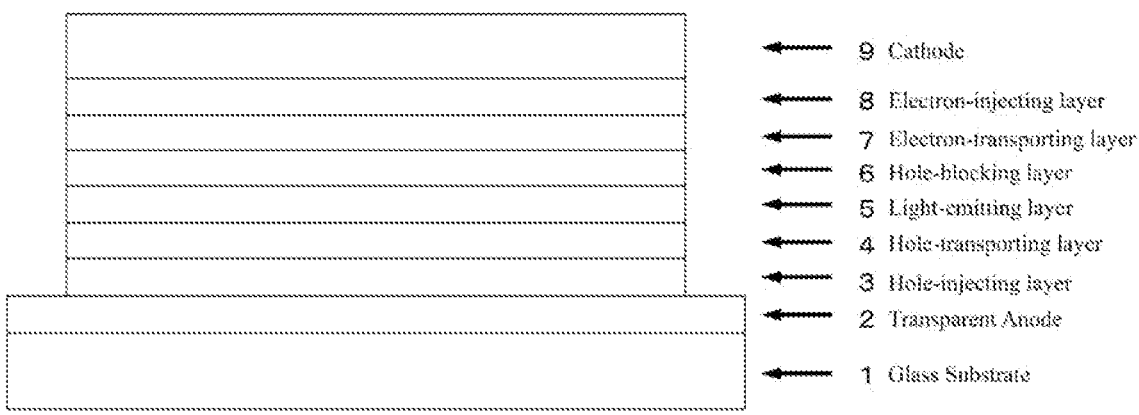
FIG. 6 is a diagram showing the configuration of organic EL elements of Examples 9 to 14 and Comparative Examples 1 and 2.

As shown in FIG. 6, an organic EL element was prepared by vapor-depositing, on an ITO electrode that was formed as a transparent anode 2 on a glass substrate 1, a hole-injecting layer 3, a hole-transporting layer 4, a light-emitting layer 5, a hole-blocking layer 6, an electron-transporting layer 7, an electron-injecting layer 8, and a cathode (aluminum electrode) 9 in this order.

Specifically, a glass substrate 1 having an ITO film with a thickness of 50 nm as a transparent anode 2 was ultrasonically cleaned in isopropyl alcohol for 20 minutes, and then dried for 10 minutes on a hot plate heated at 200° C. After that, UV/ozone treatment was performed for 15 minutes. Then, the glass substrate with ITO was set inside a vacuum vapor deposition machine, and the pressure was reduced to 0.001 Pa or less. Subsequently, an electron acceptor (Acceptor-1) having the structural formula below and a compound (HTM-1) having the structural formula below were vapor-deposited so as to coat the transparent anode 2 through binary vapor deposition at vapor deposition rates such that the ratio of the vapor deposition rate of Acceptor-1 to that of HTM-1 was 3:97, to thereby form a hole-injecting layer 3 with a thickness of 10 nm.

On this hole-injecting layer 3, a hole-transporting layer 4 (thickness: 60 nm) made of the compound (HTM-1) having the structural formula below was formed.

A compound (EMD-1) having the structural formula below and a compound (EMH-1) having the structural formula below were vapor-deposited on this hole-transporting layer 4 through binary vapor deposition at vapor deposition rates such that the ratio of the vapor deposition rate of EMD-1 to that of EMH-1 was 5:95, to thereby form a light-emitting layer 5 with a thickness of 20 nm.

Inventive Compound (5) of Example 1 and a compound (ETM-1) having the structural formula below were vapor-deposited on this light-emitting layer 5 through binary vapor deposition at vapor deposition rates such that the ratio of the vapor deposition rate of Compound (5) to that of ETM-1 was 50:50, to thereby form a layer (thickness 30 nm) serving as both a hole-blocking layer 6 and an electron-transporting layer 7.

On this layer serving as both the hole-blocking layer 6 and the electron-transporting layer 7, an electron-injecting layer 8 (thickness 1 nm) made of lithium fluoride was formed.

Finally, aluminum was vapor-deposited to a thickness of 100 nm to thereby form a cathode 9.

The prepared organic EL element was characterized in the atmosphere at normal temperature. Table 1 collectively shows the measurement results of light emission characteristics when a DC voltage was applied to the prepared organic EL element.

[Chem. 17]

(Acceptor-1)

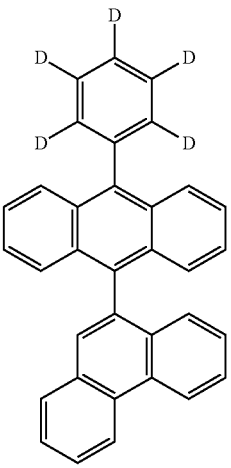

(HTM-1)

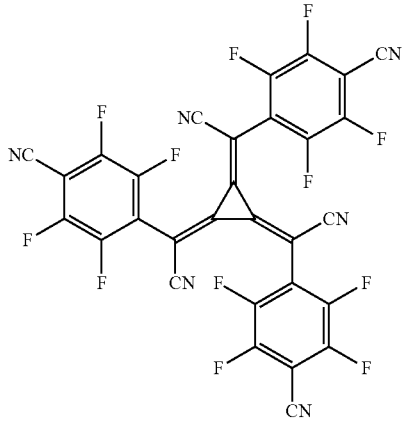

[Chem. 18]

(EMD-1)

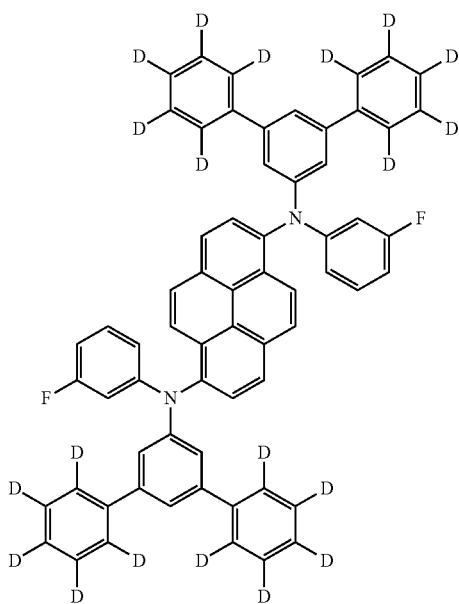

(EMH-1)

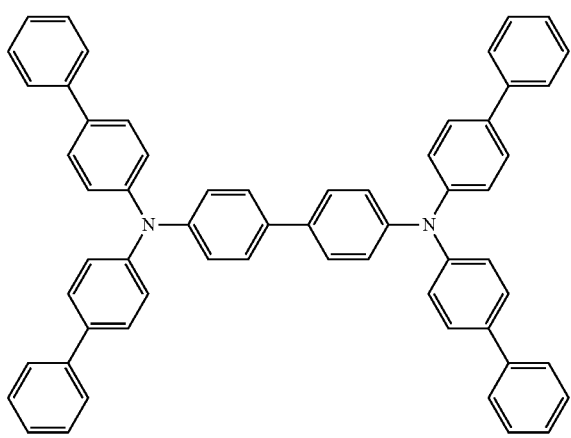

[Chem. 19]

(5)

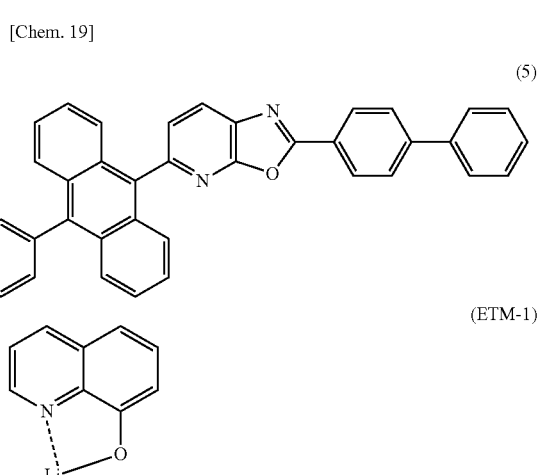

(ETM-1)

Example 10

An organic EL element was prepared under the same conditions as in Example 9, except that, instead of Compound (5) of Example 1, Compound (15) of Example 2 was used as the material of the layer serving as both the hole-blocking layer 6 and the electron-transporting layer 7, and that the binary vapor deposition was performed at vapor deposition rates such that the ratio of the vapor deposition rate of Compound (15) to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 20]

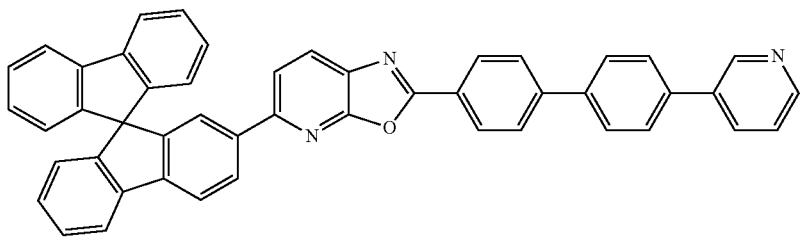

(15)

Example 11

An organic EL element was prepared under the same conditions as in Example 9, except that, instead of Compound (5) of Example 1, Compound (17) of Example 3 was used as the material of the layer serving as both the hole-blocking layer 6 and the electron-transporting layer 7, and that the binary vapor deposition was performed at vapor deposition rates such that the ratio of the vapor deposition rate of Compound (17) to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 21]

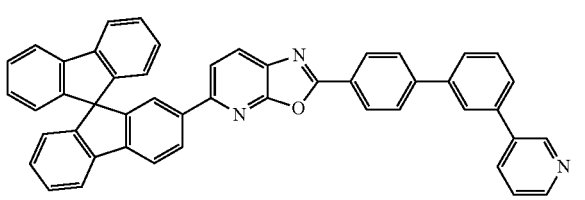

(17)

Example 12

An organic EL element was prepared under the same conditions as in Example 9, except that, instead of Compound (22) of Example 1, Compound (22) of Example 4 was used as the material of the layer serving as both the hole-blocking layer 6 and the electron-transporting layer 7, and that the binary vapor deposition was performed at vapor deposition rates such that the ratio of the vapor deposition rate of Compound (22) to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 22]

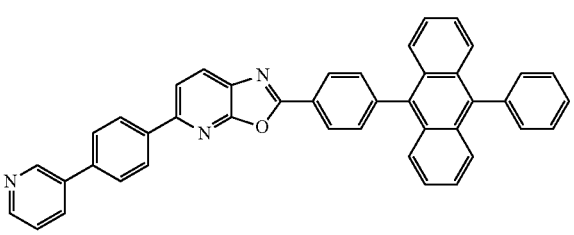

(22)

Example 13

An organic EL element was prepared under the same conditions as in Example 9, except that, instead of Compound (5) of Example 1, Compound (26) of Example 5 was used as the material of the layer serving as both the hole-blocking layer 6 and the electron-transporting layer 7, and that the binary vapor deposition was performed at vapor deposition rates such that the ratio of the vapor deposition rate of Compound (26) to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 23]

(26)

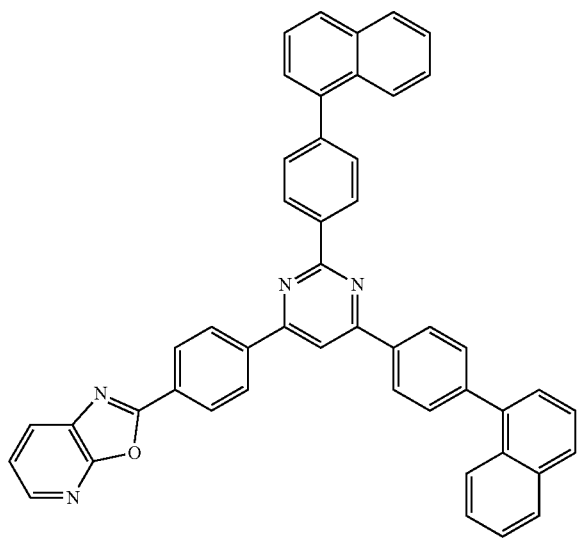

Example 14

An organic EL element was prepared under the same conditions as in Example 9, except that, instead of Compound (5) of Example 1, Compound (30) of Example 6 was used as the material of the layer serving as both the hole-blocking layer 6 and the electron-transporting layer 7, and that the binary vapor deposition was performed at vapor deposition rates such that the ratio of the vapor deposition rate of Compound (30) to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 24]

(30)

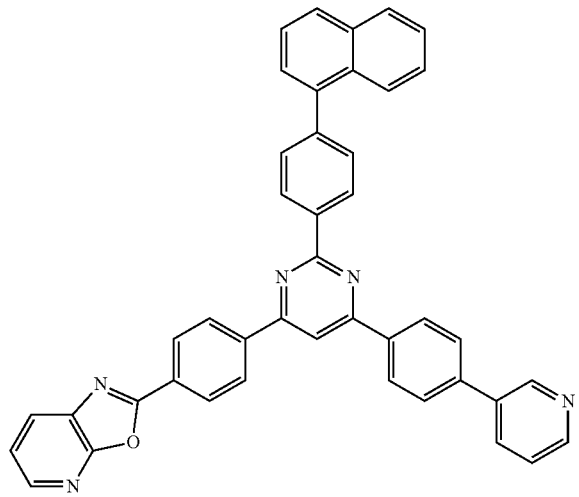

Comparative Example 1

For comparison, an organic EL element was prepared under the same conditions as in Example 9, except that, instead of Compound (5) of Example 1, a compound (ETM-2) having the structural formula below (see Patent Literature 5, for example) was used as the material of the layer serving as both the hole-blocking layer 6 and the electron-transporting layer 7, and that the binary vapor deposition was performed at vapor deposition rates such that the ratio of the vapor deposition rate of ETM-2 to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 25]

(ETM-2)

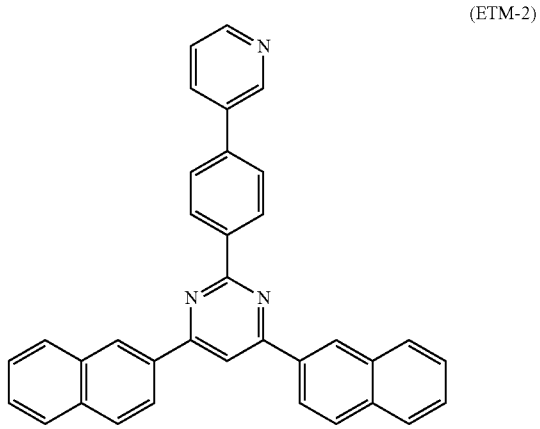

Comparative Example 2

For comparison, an organic EL element was prepared under the same conditions as in Example 9, except, instead of Compound (5) of Example 1, a compound (ETM-3) having the structural formula below (see Patent Literature 7, for example) was used as the material of the layer serving as both the hole-blocking layer 6 and the electron-transporting layer 7, and that the binary vapor deposition was performed at vapor deposition rates such that the ratio of the vapor deposition rate of ETM-3 to that of ETM-1 was 50:50. The prepared organic EL element was characterized in the atmosphere at normal temperature. Table 3 collectively shows the measurement results of light emission characteristics when a DC voltage was applied to the prepared organic EL element.

[Chem. 26]

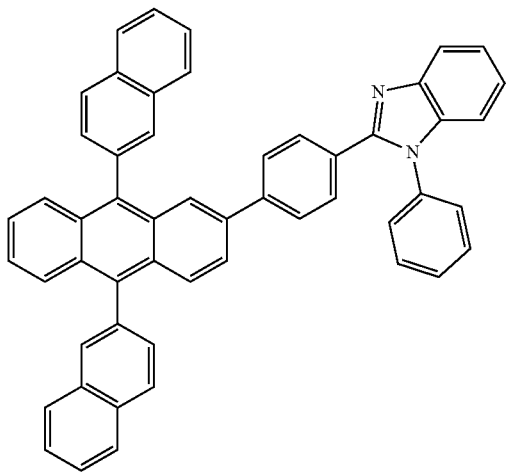

(ETM-3)

The element lifespan of each of the organic EL elements prepared in Examples 9 to 14 and Comparative Examples 1 and 2 was measured. Table 3 collectively shows the results. The element lifespan was determined as follows: the organic EL element was driven by constant current to emit light at an initial luminance (luminance when light emission started) of 2,000 cd/m$^2$, and the time taken for the luminance to decay to 1,900 cd/m$^2$ (corresponding to 95% based on the initial luminance (100%): 95% decay) was determined and defined as the element lifespan.

TABLE 3

| | Layer serving as both hole locking layer and electron-transporting layer | Voltage [V] (@10 mA/cm$^2$) | Luminance [cd/m$^2$] (@10 mA/cm$^2$) | Luminous efficacy [cd/A] (@10 mA/cm$^2$) | Power efficiency [lm/W] (@10 mA/cm$_2$) | Element lifespan (95% decay) |
|---|---|---|---|---|---|---|
| Ex. 9 | Compound (5)/ETM-1 | 3.53 | 861 | 8.62 | 7.69 | 257 hrs. |
| Ex. 10 | Compound (15)/ETM-1 | 3.54 | 876 | 8.76 | 7.79 | 267 hrs. |
| Ex. 11 | Compound (17)/ETM-1 | 3.44 | 874 | 8.75 | 8.00 | 266 hrs. |
| Ex. 12 | Compound (22)/ETM-1 | 3.48 | 871 | 8.72 | 7.87 | 252 hrs. |
| Ex. 13 | Compound (26)/ETM-1 | 3.50 | 866 | 8.68 | 7.81 | 293 hrs. |
| Ex. 14 | Compound (30)/ETM-1 | 3.52 | 880 | 8.81 | 7.87 | 285 hrs. |
| Com. Ex. 1 | ETM-2/ETM-1 | 3.82 | 805 | 8.05 | 6.62 | 165 hrs. |
| Com. Ex. 2 | ETM-3/ETM-1 | 4.01 | 659 | 6.59 | 5.16 | 203 hrs. |

As shown in Table 3, a current of 10 mA/cm$^2$ in terms of a current density was passed through the organic EL elements, and at that time, while the organic EL elements of Comparative Examples 1 and 2 including the compounds ETM-2 and 3 of the structural formulas shown above, respectively, had a driving voltage of 3.82 to 4.01 V, the organic EL elements of Examples 9 to 14 had a lower driving voltage of 3.44 to 3.54 V. While the organic EL elements of Comparative Examples 1 and 2 had a luminous efficacy of 6.59 to 8.05 cd/A, the organic EL elements of Examples 9 to 14 had an improved luminous efficacy of 8.62 to 8.81 cd/A. While the organic EL elements of Comparative Examples 1 and 2 had a power efficiency of 5.16 to 6.62 lm/W, the organic EL elements of Examples 9 to 14 had a significantly improved power efficiency of 7.69 to 8.00 lm/W. While the organic EL elements of Comparative Examples 1 and 2 had an element lifespan (95% decay) of 165 to 203 hours, the organic EL elements of Examples 9 to 14 had a significantly longer lifespan of 252 to 293 hours.

As described above, it is seen that the organic EL elements of the present invention had excellent luminous efficacy and power efficiency as well as a long lifespan, compared with the elements including the compounds ETM-2 or 3 of the structural formula shown above.

INDUSTRIAL APPLICABILITY

The compound having a specific azabenzoxazole ring structure of the present invention has good electron-injecting properties and excellent hole-blocking capability and is stable in the form of a thin film, and the compound of the present invention is therefore an excellent compound for an organic EL element. An organic EL element prepared by using this compound can achieve high efficiency and also achieve a reduced driving voltage and hence improved durability. Thus, the organic EL element can be applied to uses such as home electric appliances and lighting equipment.

The invention claimed is:

1. A compound having an azabenzoxazole ring structure and being represented by the general formula (a-2):

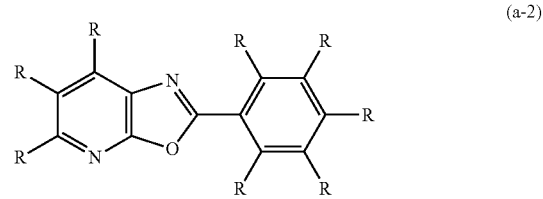

(a-2)

where R is the same or different, and each represents a group represented by the structural formula below, a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted fused polycyclic aromatic group, a linear or branched alkyl group having 1 to 6 carbon atoms and optionally having a substituent, a cycloalkyl group having 5 to 10 carbon atoms and optionally having a substituent, a linear or branched alkenyl group having 2 to 6 carbon atoms and optionally having a substituent, a linear or branched alkyloxy group having 1 to 6 carbon atoms and optionally having a substituent, or a cycloalkyloxy group having 5 to 10 carbon atoms and optionally having a substituent;

provided that at least one R is a group represented by the structural formula below,

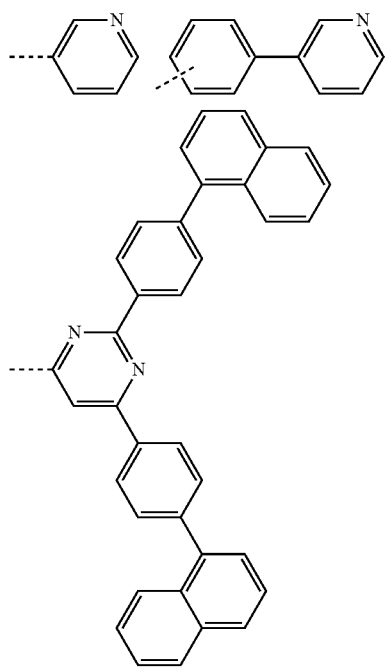

-continued

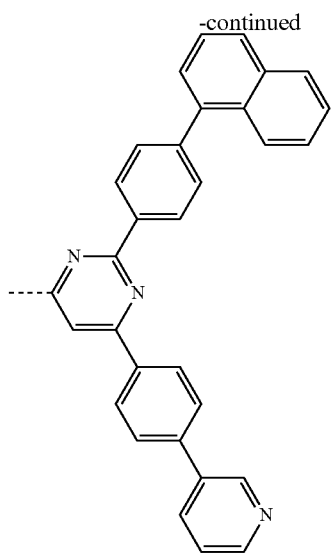

and the dashed line represents a binding site.

2. An organic electroluminescent element comprising a pair of electrodes and one or more organic layers sandwiched therebetween,
wherein the compound having an azabenzoxazole ring structure according to claim 1 is included in at least one of the organic layers as a constituent material thereof.

3. The organic electroluminescent element according to claim 2,
wherein the organic layer including the compound having an azabenzoxazole ring structure is an electron-transporting layer.

4. The organic electroluminescent element according to claim 2,
wherein the organic layer including the compound having an azabenzoxazole ring structure is a hole-blocking layer.

5. The organic electroluminescent element according to claim 2,
wherein the organic layer including the compound having an azabenzoxazole ring structure is a light-emitting layer.

6. The organic electroluminescent element according to claim 2,
wherein the organic layer including the compound having an azabenzoxazole ring structure is an electron-injecting layer.

* * * * *